US010689702B2

(12) United States Patent
Chan et al.

(10) Patent No.: US 10,689,702 B2
(45) Date of Patent: Jun. 23, 2020

(54) BIOMARKERS FOR DIABETES

(71) Applicant: The Chinese University of Hong Kong, Shatin, New Territories (CN)

(72) Inventors: Juliana Chung-Ngor Chan, Tai Po (CN); Wing-Yee So, Kowloon (CN); Ronald Ching-Wan Ma, Hong Kong (CN)

(73) Assignee: The Chinese University of Hong Kong, Shatin, N.T., Hong Kong SAR (CN)

(*) Notice: Subject to any disclaimer, the term of this patent is extended or adjusted under 35 U.S.C. 154(b) by 0 days.

(21) Appl. No.: 14/372,985

(22) PCT Filed: Jan. 28, 2013

(86) PCT No.: PCT/CN2013/071053
§ 371 (c)(1),
(2) Date: Jul. 17, 2014

(87) PCT Pub. No.: WO2013/110245
PCT Pub. Date: Aug. 1, 2013

(65) Prior Publication Data
US 2015/0045238 A1 Feb. 12, 2015

Related U.S. Application Data

(60) Provisional application No. 61/591,598, filed on Jan. 27, 2012.

(51) Int. Cl.
*C12Q 1/68* (2018.01)
*C12P 19/34* (2006.01)
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/106* (2013.01); *C12Q 2600/118* (2013.01); *C12Q 2600/156* (2013.01); *C12Q 2600/16* (2013.01)

(58) Field of Classification Search
CPC ............ C12Q 1/6883; C12Q 2600/106; C12Q 2600/118; C12Q 2600/156
See application file for complete search history.

(56) References Cited

FOREIGN PATENT DOCUMENTS

| WO | 00/23784 A2 | 4/2000 |
|----|-------------|--------|
| WO | 2005/099335 A2 | 10/2005 |
| WO | 2008/065544 A2 | 6/2008 |

OTHER PUBLICATIONS

Submitted SNP(ss) Details: ss160789624 (Aug. 4, 2009) from http://www.ncbi.nlm.nih.gov, pp. 1-2.*
Submitted SNP(ss) Details: ss160376259 (Aug. 4, 2009) from http://www.ncbi.nlm.nih.gov, pp. 1-2.*
SNP linked to Gene (geneID:1363) Via Contig Annotation, from www.ncbi.nlm.nih.gov, printed on Feb. 22, 2016, p. 1 provided.*
Chen, H. et al. Human Mutation (2001) 18:120-131.*
Utsunomiya N. et al. Diabetologia (1998) 41: 701-705.*
Juppner H. Bone vol. 17, No. 2, Supplement, Aug. 1995:39S-42S.*
Hegele R.A. Arterioscler Thromb Vasc Biol. 2002;22:1058-1061.*
Pennisi E. Science; Sep. 18, 1998; 281, 5384, pp. 1787-1789.*
Lam, Kwok Lim "Genetic Association of Islet Amyloid Polypeptide (IAPP) Encoding Pathways in Pancreatic Beta-Cells with Type 2 Diabetes Complemented by Functional Study". Thesis from the Chinese University of Hong Kong, Oct. 2010, 196 printed pages.*
Zinman, B. et al. The Lancet, vol. 376 Jul. 10, 2010, p. 103-111.*
Jia, et al., "Association of the mutation for the human carboxypeptidase E gene exon 4 with the severity of coronary artery atherosclerosis," *Mol Biol Rep.*, vol. 36, Issue 2, pp. 245-254 (2009).
Kwak, et al., "Association of polymorphisms in the insulin-degrading enzyme gene with type 2 diabetes in the Korean population," *Diabetes Research and Clinical Practice*, vol. 79, Issue 2, pp. 284-290 (2008).
International Search Report for International Application No. PCT/CN2013/071053 dated May 9, 2013.

* cited by examiner

*Primary Examiner* — Stephen T Kapushoc
(74) *Attorney, Agent, or Firm* — Kilpatrick Townsend & Stockton LLP

(57) ABSTRACT

The present invention provides a method for assessing the presence and risk of developing type 2 diabetes, cancer of all sites, or cardiovascular disease in a subject by detecting sequence variation in one or more genes such as carboxypeptidase E (CPE) and insulin degradation enzyme (IDE). A kit, array, and device useful for such a method are also provided. In addition, the present invention provides a method for treating type 2 diabetes, cancer of all sites, or cardiovascular disease in patients who have been tested and shown to have the pertinent genetic variations.

11 Claims, 22 Drawing Sheets
Specification includes a Sequence Listing.

Figure 1. Overall Premise

1. People with family history of diabetes may harbor genetic variants which increase risk of diabetes (McCarthy. *N Engl J Med*;363:2339-50, 2010).
2. People with low body mass index (BMI), especially in Asian populations, often have low beta cell reserve (Chan WB *et al Diabet Med* 21:349-53, 2004).
3. Dysregulation of human islet amyloid polypeptide (IAPP) pathway with abnormal processing (e.g. CPE gene) and degradation (IDE gene) of IAPP may lead to excessive oligomerization to cause mitochondrial dysfunction and ER stress leading to oxidative stress and beta cell death (see text)
4. Loss of beta cell function leads to hyperglycemia which can activate multiple pathways including but not limited to the renin angiotensin system. The associated insufficient insulin action can lead to dysregulation of the IGF1-SREBP-HMG coA reductase pathway. Activation of these pathways are known to cause dysregulation of cell signaling leading to abnormal cell cycle with increased cancer risk (Yang *et al, Diabetes* 58:1518-25, 2009).
5. People with diabetes are at high risk for cardiovascular (CVD) and renal disease which can increase the risk of each other in a reciprocal manner (see text)
6. The risks for cancer, CVD, renal disease and related death are amplified in subjects with risk factors including but not limited to genetic variants for diabetes and CVD and external stressors such as chronic hepatitis B infection (see text)

Testing for genetic variants associated with diabetes and CVD using *CPE/IDE* as examples, especially in subjects with positive family history, low BMI, chronic hepatitis B infection will identify high risk subjects for cancer, CVD and renal disease who will benefit from early intervention including but not limited to use of blood glucose lowering drugs, HMGcoA reductase inhibitors (e.g. statins) and blockers of renin angiotensin system (e.g. ACEI and ARB).

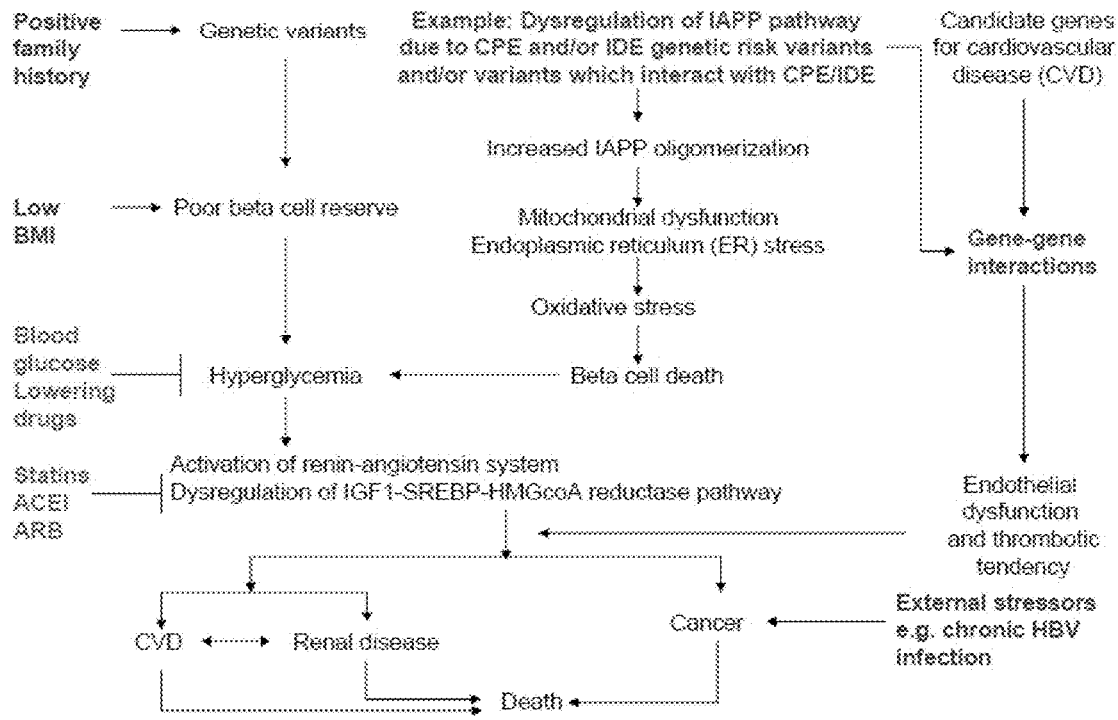

Figure 2 The risk association of type 2 diabetes (T2D) with a genetic risk score (GRS) in all Asian subjects analyzed by logistic regression (LR) analysis with adjustment for "Study Population" encoding individual unrelated case-control cohorts of the stage-1 Hong Kong Chinese, the stage-2 Hong Kong Chinese, Shanghai Chinese, Japanese and Korean as 1 to 5 respectively. Each risk allele of rs1583645 (*CPE*) and rs6583813 (*IDE*) was given a GRS of 1 under additive models. Increasing GRS was associated with a trend of increasing risk for type 2 diabetes (T2D) (P adjusted <0.001) with the highest GRS of 4 conferring an odds ratio of 1.45 compared to the lowest GRS of 0 (P adjusted =0.02*).

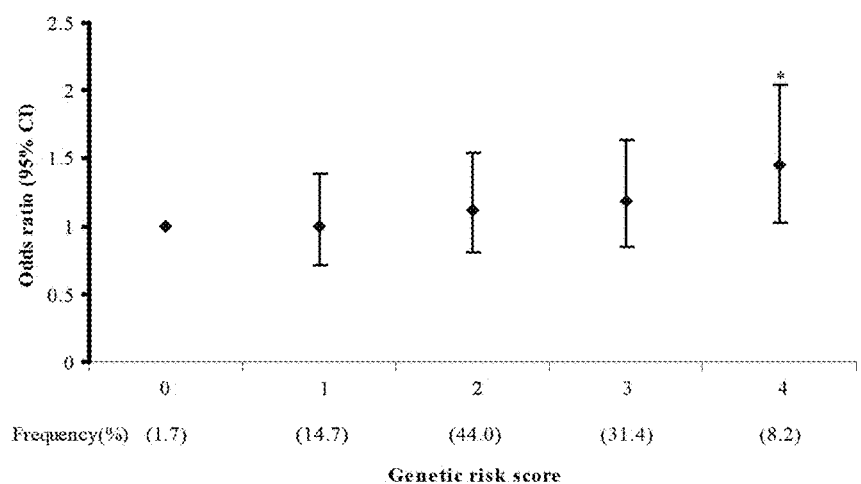

Figure 3 (A) Plasma islet amyloid polypeptide (IAPP) and (B) molar ratio of IAPP to insulin (IAPP/INS) in 85 unrelated non-diabetic controls selected from a family-based cohort categorized by genetic risk scores (GRS) (1 risk allele of rs1583645 of CPE and rs6583813 of IDE genes each given 1 point). Plasma IAPP (*P=0.008) and IAPP/INS ratio (†P = 0.006) increased with increasing GRS.
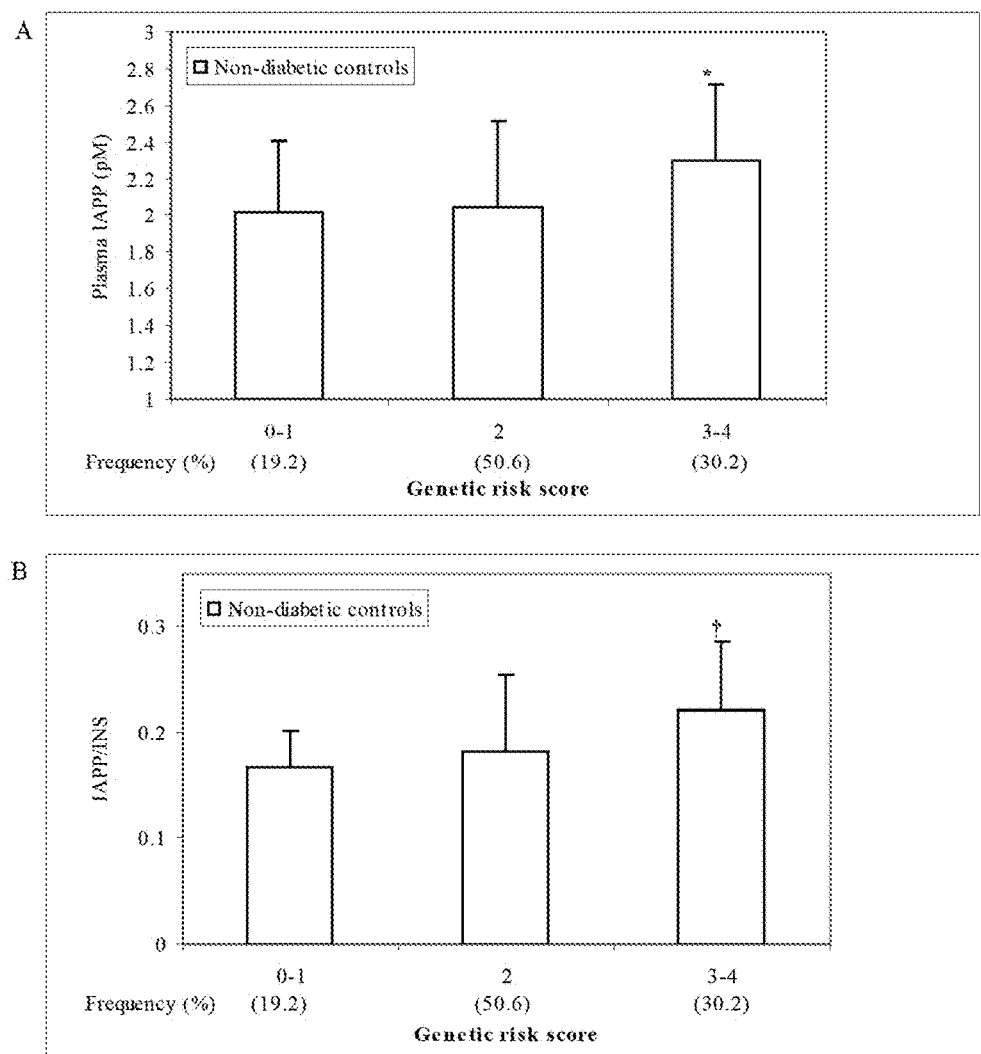

Figure 4 Overall hypothesis. Genetic variations in IAPP encoding pathways including maturation, degradation and stabilization might be associated with type 2 diabetes (T2D) and beta-cell dysfunction through increased formation of Pro-IAPP or IAPP, oligomerization and reduced clearance of IAPP.

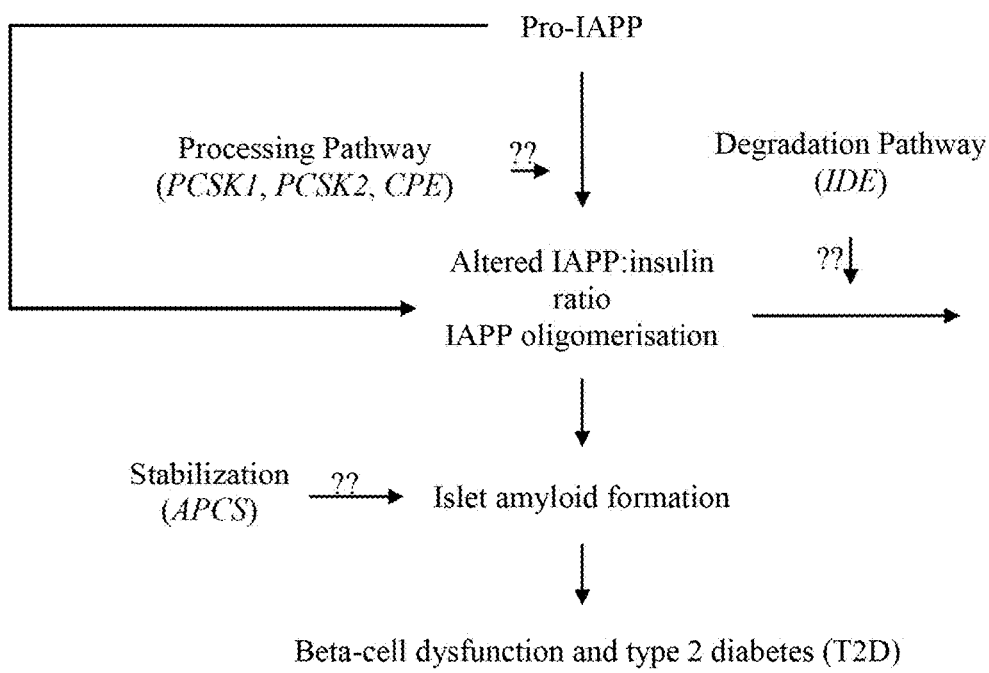

Key:

Carboxypeptidase E (*CPE*)
Insulin degrading enzyme (*IDE*)
Islet amyloid polypeptide (*IAPP*)
Prohormone convertase 1 (*PCSK1*)
Prohormone convertase 2 (*PCSK2*)
Serum P amyloid component (*APCS*)

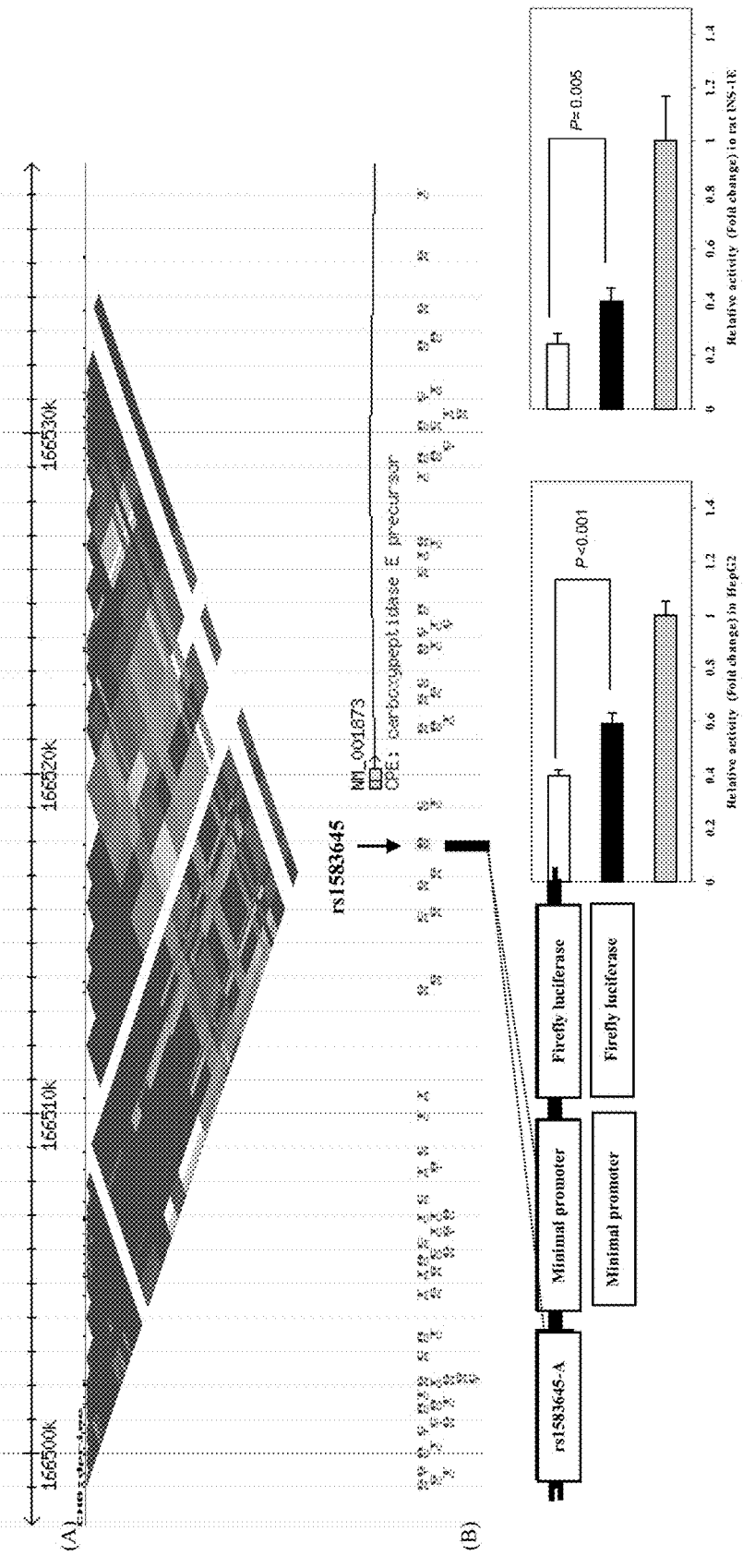

Figure 5 Effect of rs1583645 A/G polymorphism on luciferase activity assays. (A) Upstream region of transcription start site (TSS), first exon and part of intron 1 of the *CPE* gene (NCBI Build36.1, CHR4:166496501-166536501). The LD structure of *CPE* SNPs within this region was shown by D' using the Chinese HapMap data. The arrow indicated the location of rs1583645. (B) *CPE*-A/G constructs consisting of 449bp of *CPE* rs1583645 region and pGL4.23 firefly luciferase reporter vectors were transfected into HepG2 and rat INS-1E cell lines together with *Renilla* luciferase reporter vectors. Measurement of the firefly luciferase activity of *CPE*-A/G constructs was normalized relative to the activity of the *Renilla* luciferase vectors. Data shown were the mean±SEM of at least three independent experiments in triplicate set up. The constructs of *CPE*-G showed 50% and 66.7% increased transcriptional activity in HepG2 and rat INS-1E cell lines respectively when compared to the constructs of *CPE*-A ($P<0.001$ and $P=0.005$ respectively by Mann-Whitney $U$-test).

Figure 6. Kaplan Miere curve showing the cumulative incidence of cancer in type 2 diabetic patients with positive family history according to their genotype of *IDE* rs6583813 under an additive model followed up for a mean period of 8 years and after adjustment for confounding variables including age, gender, disease duration, smoking, waist, systolic blood pressure, glycated hemoglobin, log triglyceride, HDL-C, LDL-C, log urinary albumin:creatinine ratio plus 1, log estimated glomerular filtratioin rate, use of lipid lowering drugs, blood pressure lowering drugs, oral blood glucose lowering drugs, insulin and ACE inhibitors and AII receptor blockers at baseline.

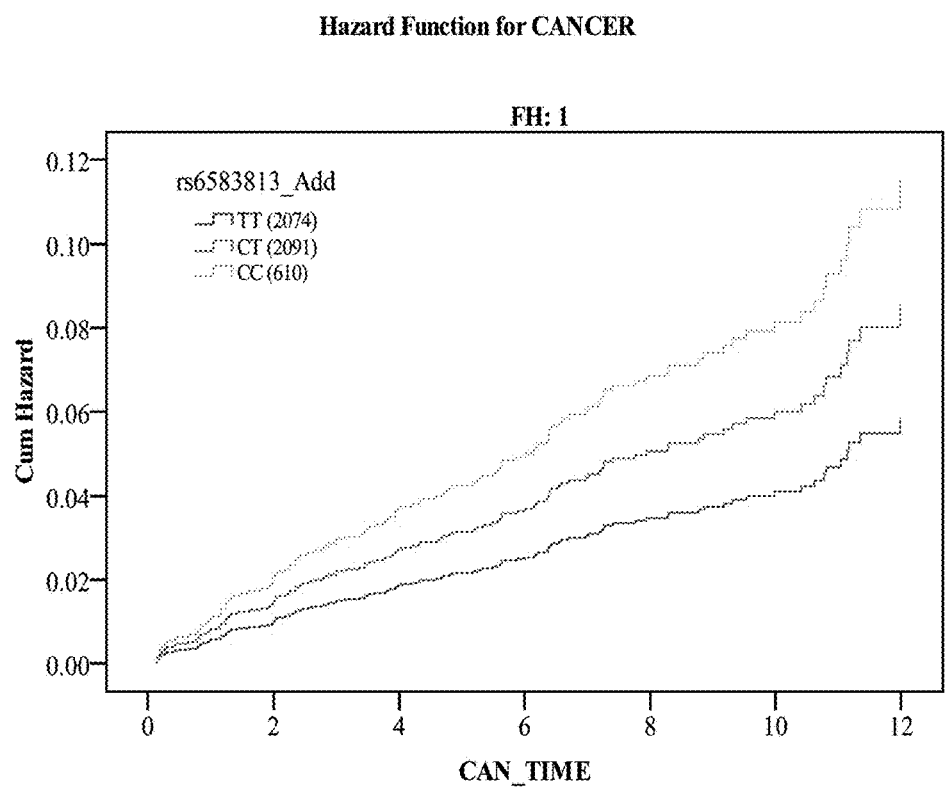

Figure 7. Kaplan Miere curve showing the cumulative incidence of cardiovascular disease in non-obese type 2 diabetic patients according to their genotype of *CPE* rs1583645 under an additive model followed up for a mean period of 8 years and after adjustment for confounding variables including age, gender, disease duration, smoking, waist, systolic blood pressure, glycated hemoglobin, log triglyceride, HDL-C, LDL-C, log urinary albumin:creatinine ratio plus 1, log estimated glomerular filtratioin rate, use of lipid lowering drugs, blood pressure lowering drugs, oral blood glucose lowering drugs, insulin and ACE inhibitors and AII receptor blockers at baseline.

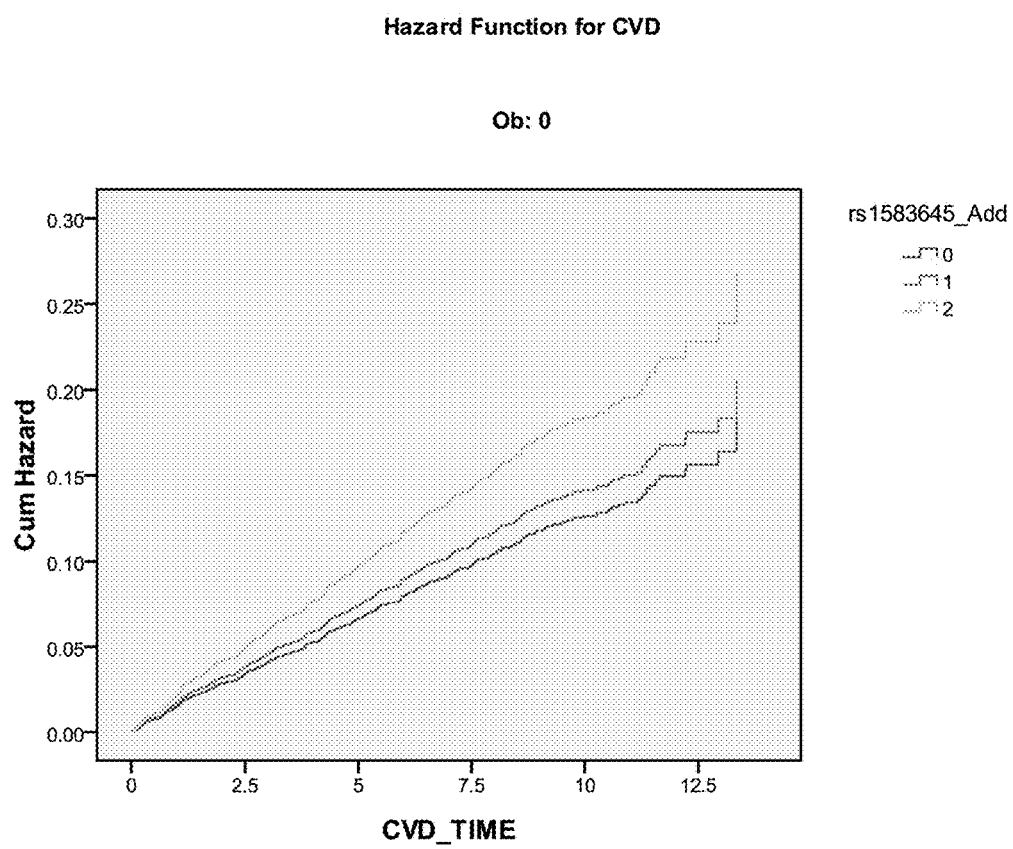

Figure 8. Kaplan Miere curve showing the cumulative incidence of cancer in type 2 diabetic patients with positive family history according to their genetic risk scores of *CPE* rs1583645 and *IDE* rs6583813 under an additive model followed up for a mean period of 8 years and after adjustment for confounding variables including age, gender, disease duration, smoking, waist, systolic blood pressure, glycated hemoglobin, log triglyceride, HDL-C, LDL-C, log urinary albumin:creatinine ratio plus 1, log estimated glomerular filtratioin rate, use of lipid lowering drugs, blood pressure lowering drugs, oral blood glucose lowering drugs, insulin and ACE inhibitors and AII receptor blockers at baseline.

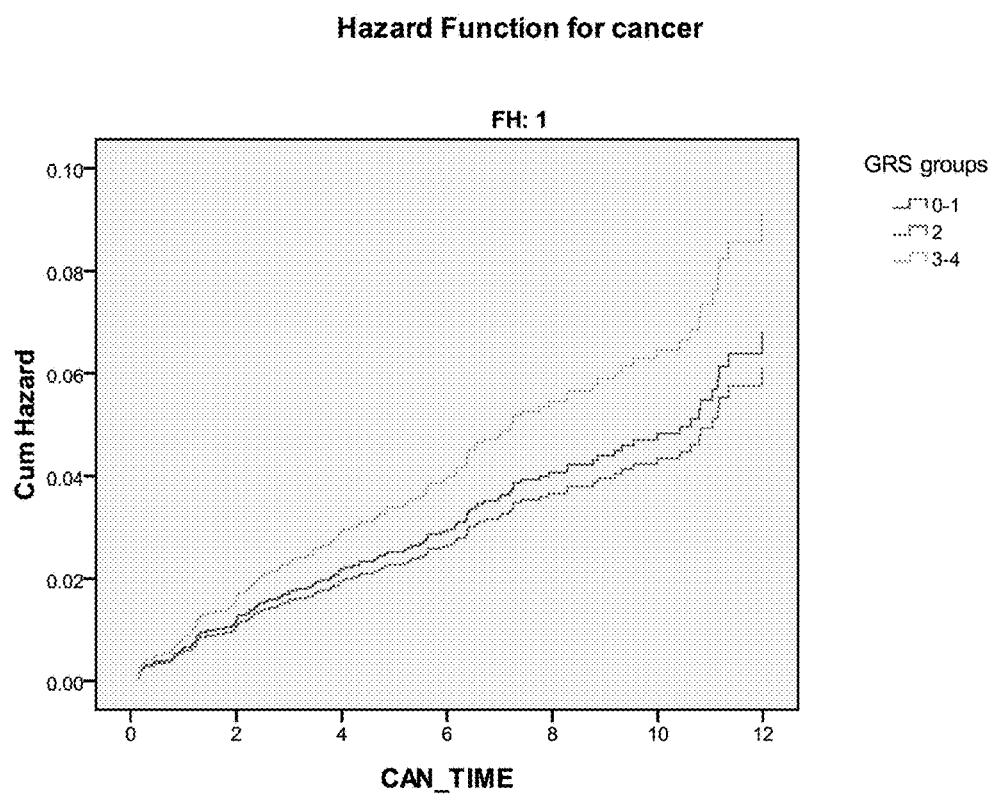

Figure 9. A Structural equation model showing that 80% of renal function variance can be explained by genotype-phenotype interactions in type 2 diabetic patients at low risk for chronic kidney disease.
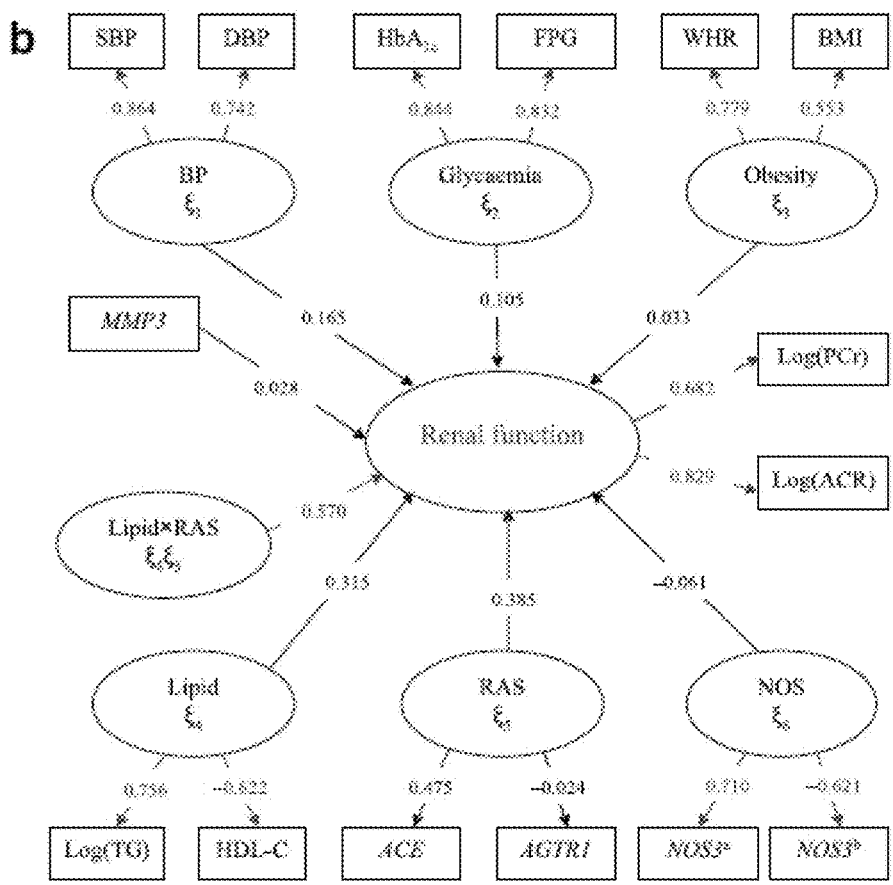

Figure 10. A Structural equation model showing that 30% of renal function variance can be explained by genotype-phenotype interactions in type 2 diabetic patients at high risk for chronic kidney disease.
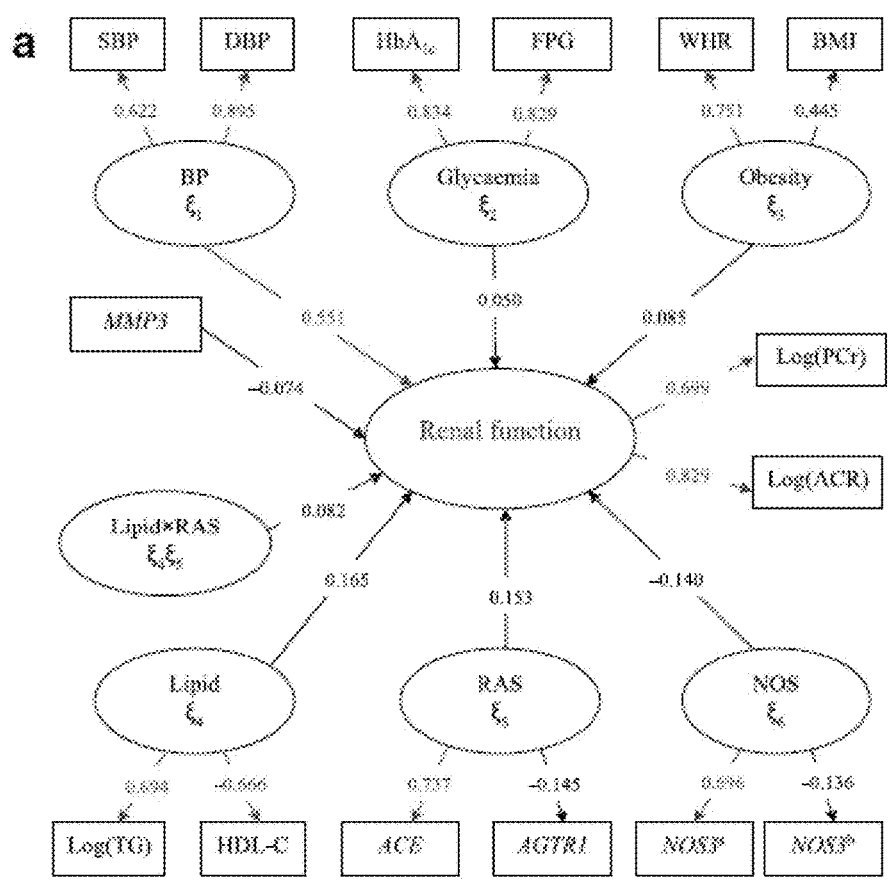

Figure 11. A Structural equation model showing the complex phenotype-genotype interactions for multiple traits including blood pressure, obesity, blood lipid and blood glucose to explain 30% of renal function in high risk subjects.
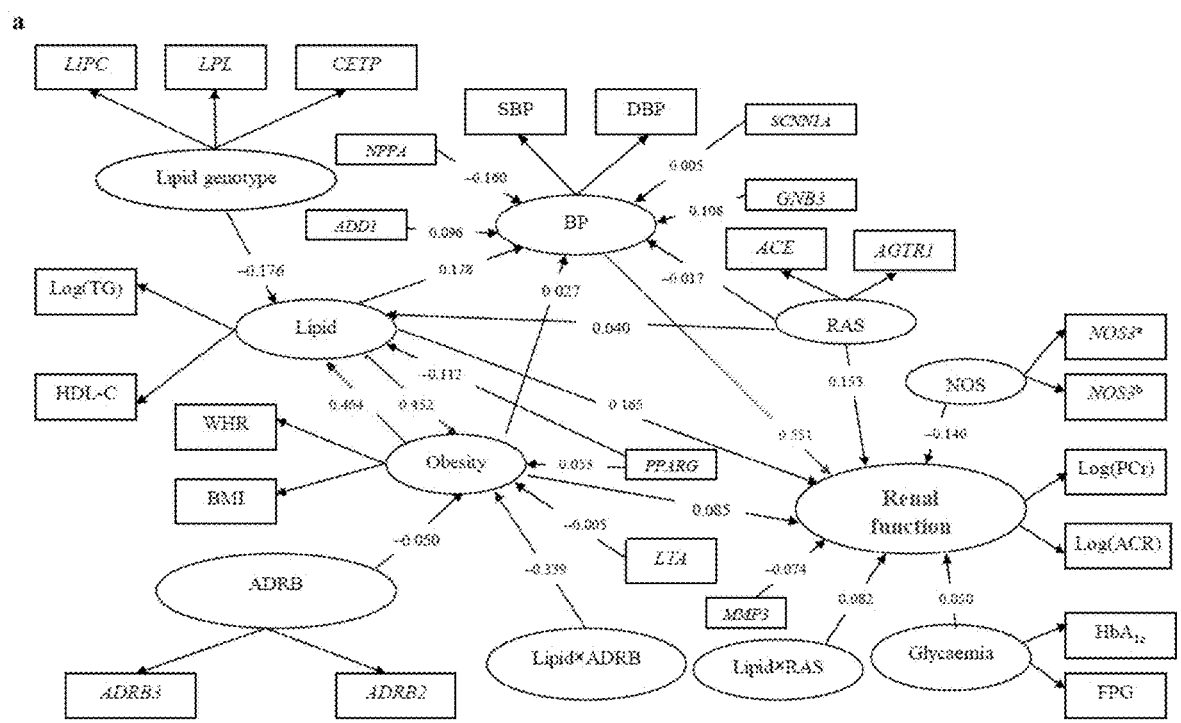

Figure 12. A Structural equation model showing the complex phenotype-genotype interactions for multiple traits including blood pressure, obesity, blood lipid and blood glucose to explain 80% of renal function in low risk subjects.
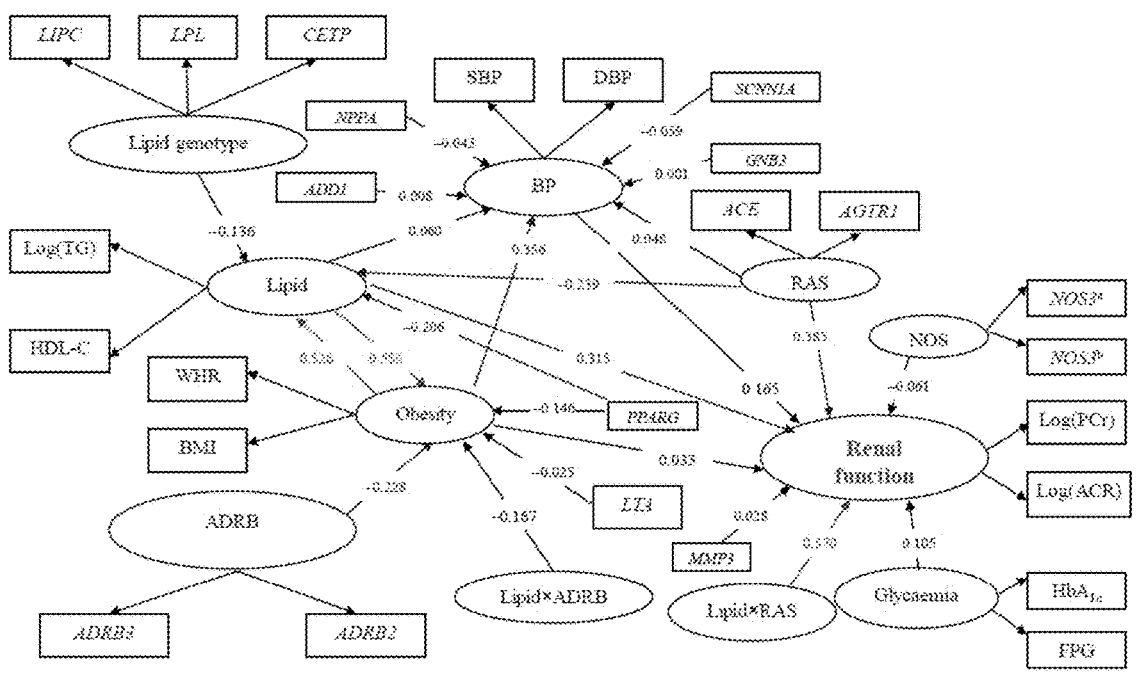

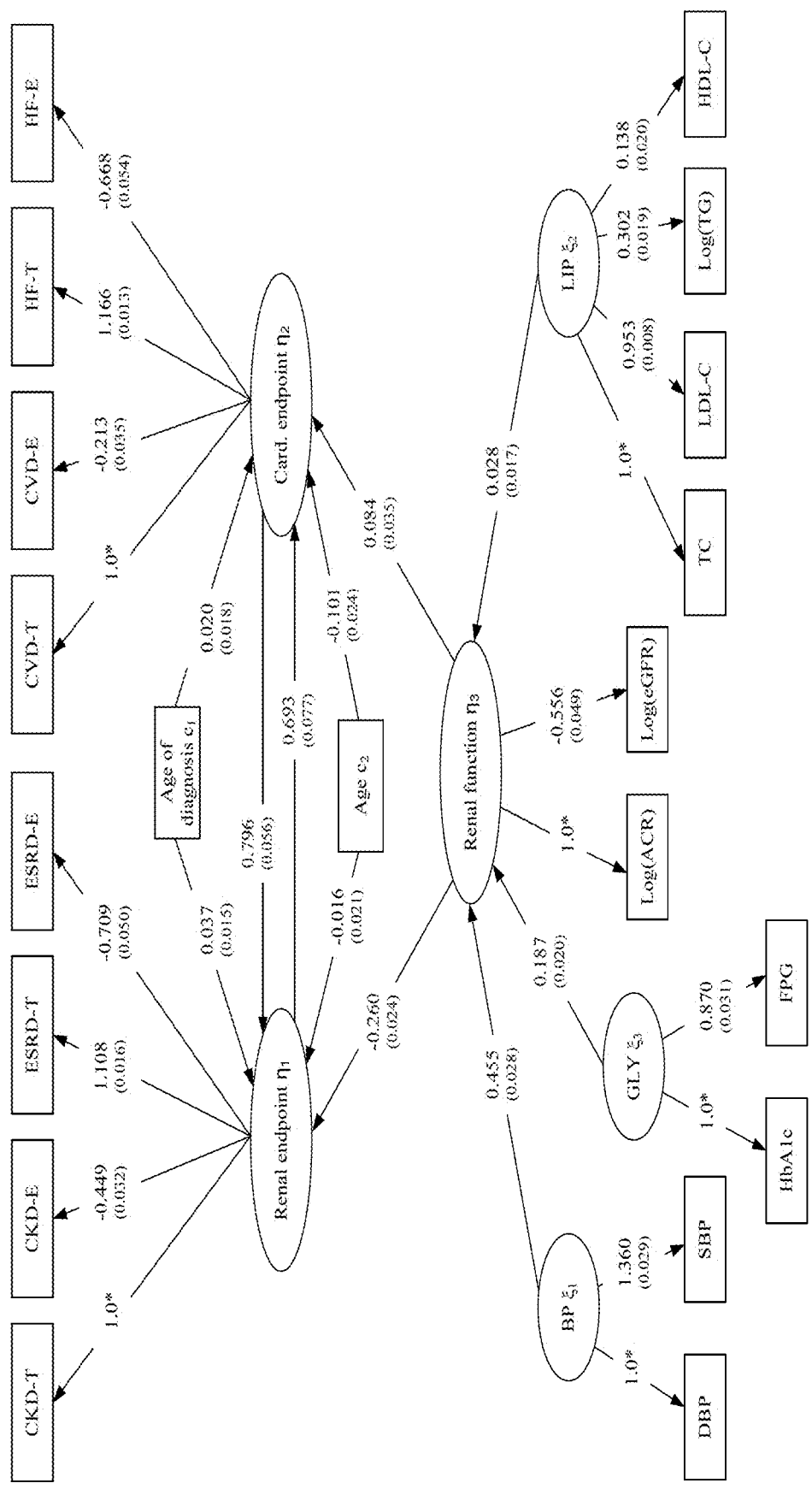
Figure 13. A structural equation model which quantifies the causal relationships between cardiovascular and renal disease which can be predicted by blood pressure, blood lipid, blood glucose, age of diagnosis, hepatitis B infection and renal function.

Figure 14. A linear association between cancer risk and HbA$_{1c}$ in a prospective cohort of 4623 Chinese type 2 diabetic patients with a mean follow up period of 5 years where every 9% increase in HbA$_{1c}$ was associated with an increased hazard ratio of 0.5 (Yang *et al Diabetes*;59:1254-60, 2010. These epidemiological observations are corroborated by a meta-analysis of intensive blood glucose lowering trials where 0.5% reduction in HbA$_{1c}$ was associated with a non-significant reduction in cancer risk by a hazard ratio of 0.5 (Johnson JL *et al, Diabetologia* doi:10.1007/s00125-010-1993-3, 2010Yang *et al Diabetologia*;54:709-710, 2011.

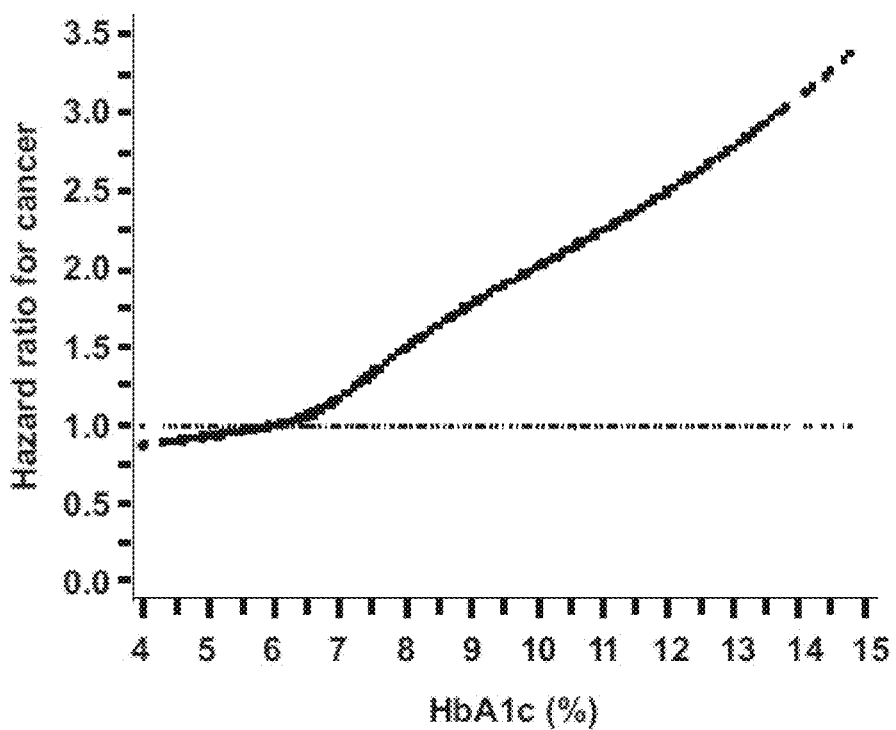

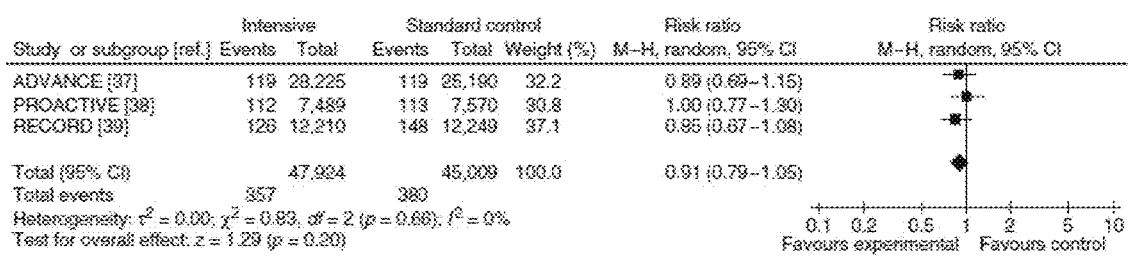

Johnston JA et al Diabetologia 2010

Figure 15. Kaplan Meier plot of the cumulative incidence of all-site cancers among patients with type 2 diabetes stratified by chronic hepatitis B viral (HBV) infection status and HbA$_{1c}$ ≥ 7.4% (P<0.0001).
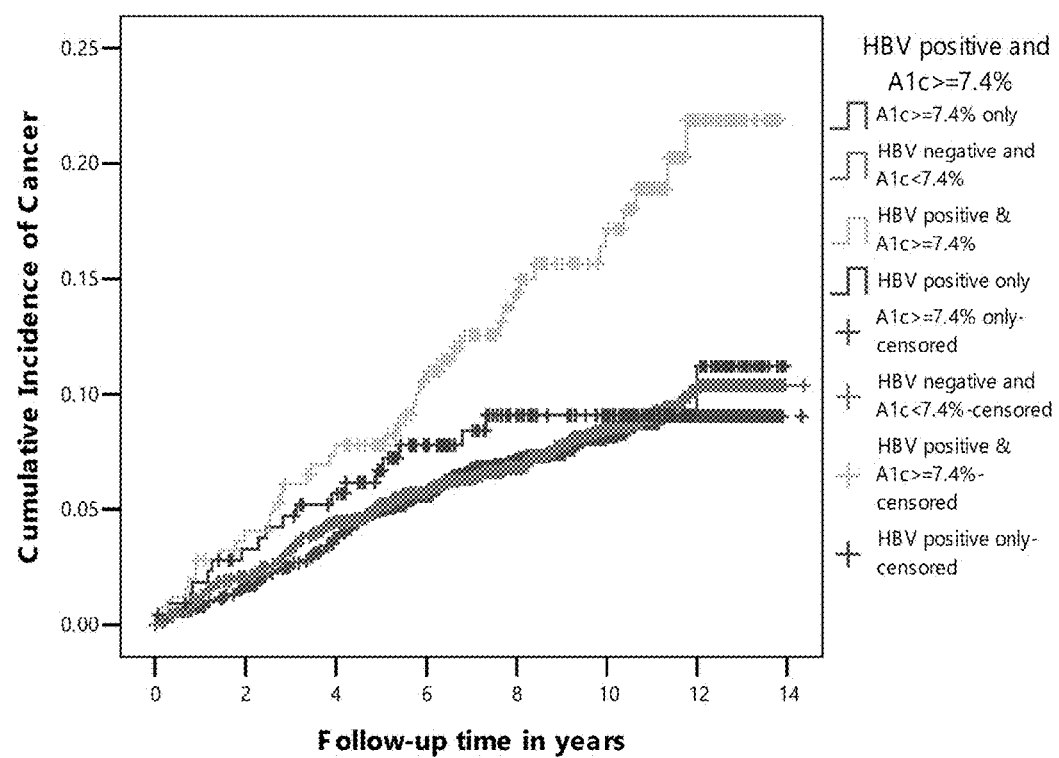

Figure 16. Use of insulin and cumulative incidence of cancer among patients with Type 2 diabetes who did not use insulin within 2.5 years prior to the enrolment (prevalent users excluded). Please refer to tables 8 and 9 for patient characteristics.

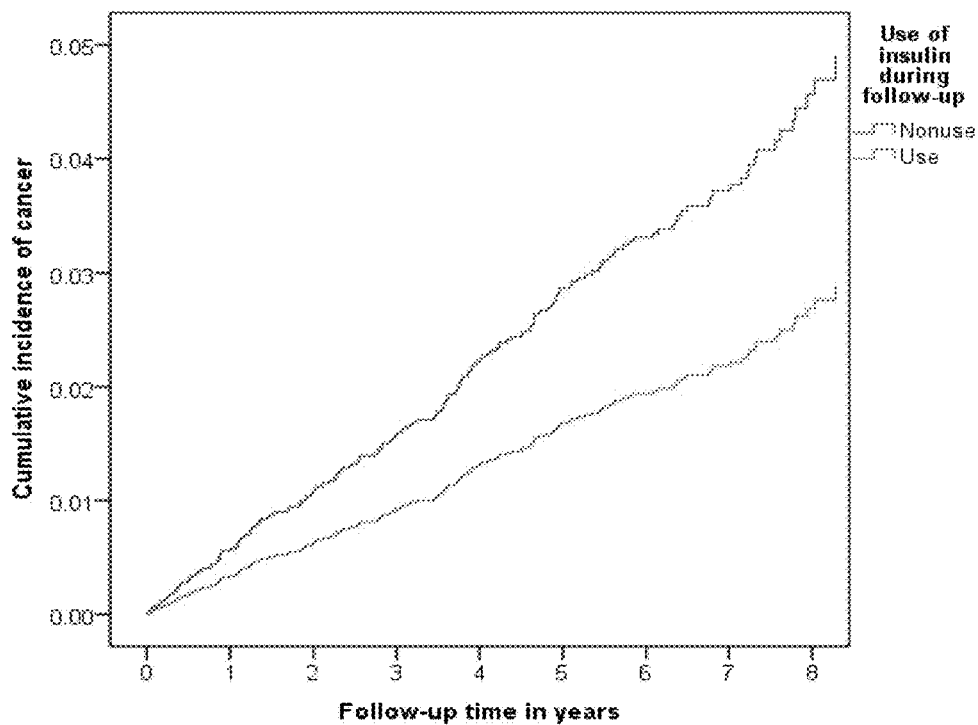

Adjusted for LDL-C related risk indicator, nonlinear associations of HDL-C and triglyceride, BMI ($<24$, $\geq 27.6$ kg/m$^2$), age, sex, occupation, use of tobacco and alcohol, duration of disease, HbA$_{1c}$, SBP, use of statins, ACEIs/ARBs, fibrates, sulphonyluria, metformin and TZDs during follow-up period, as well as propensity scores of use of insulin during follow-up period.

Figure 17. Use of metformin and cumulative incidence of cancer among patients with Type 2 diabetes who did not use metformin within 2.5 years prior to the enrolment (prevalent users excluded). Please refer to tables 8 and 9 for patient characteristics.

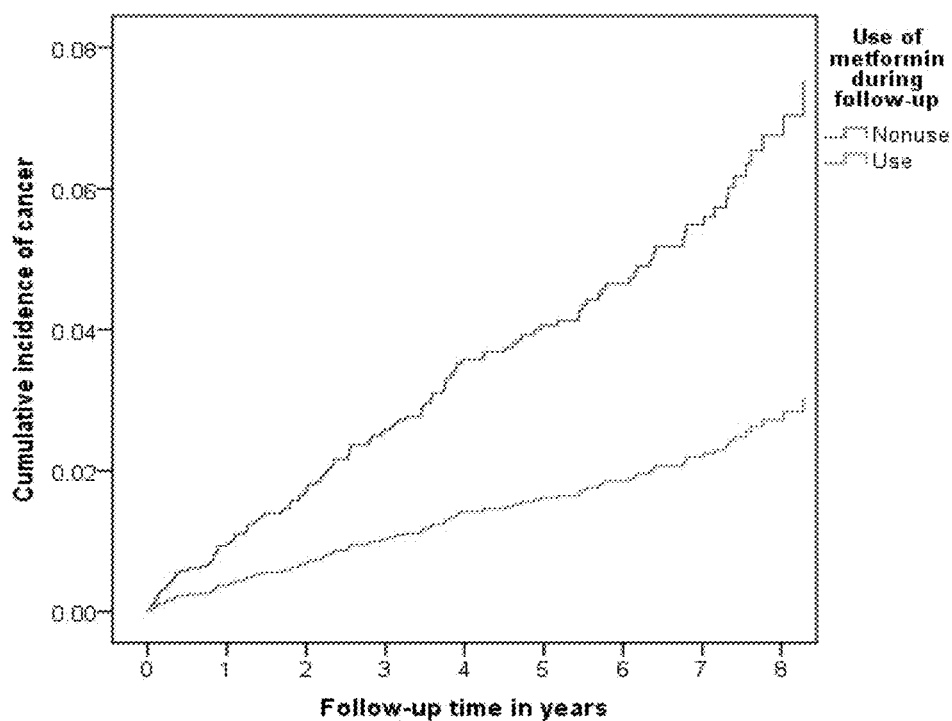

Adjusted for LDL-C related risk indicator, nonlinear associations of HDL-C and triglyceride, BMI (<24, ≥27.6 kg/m$^2$), age, sex, occupation, use of tobacco and alcohol, duration of disease, HbA$_{1c}$, SBP, use of statins, ACEIs/ARBs, fibrates, sulphonyluria, insulin and TZDs during follow-up period, as well as propensity scores of use of metformin during follow-up period.

Figure 18. Use of sulphonylurea and cumulative incidence of cancer among patients with Type 2 diabetes who did not use sulphonylurea within 2.5 years prior to the enrolment (prevalent users excluded). Please refer to tables 8 and 9 for patient characteristics.

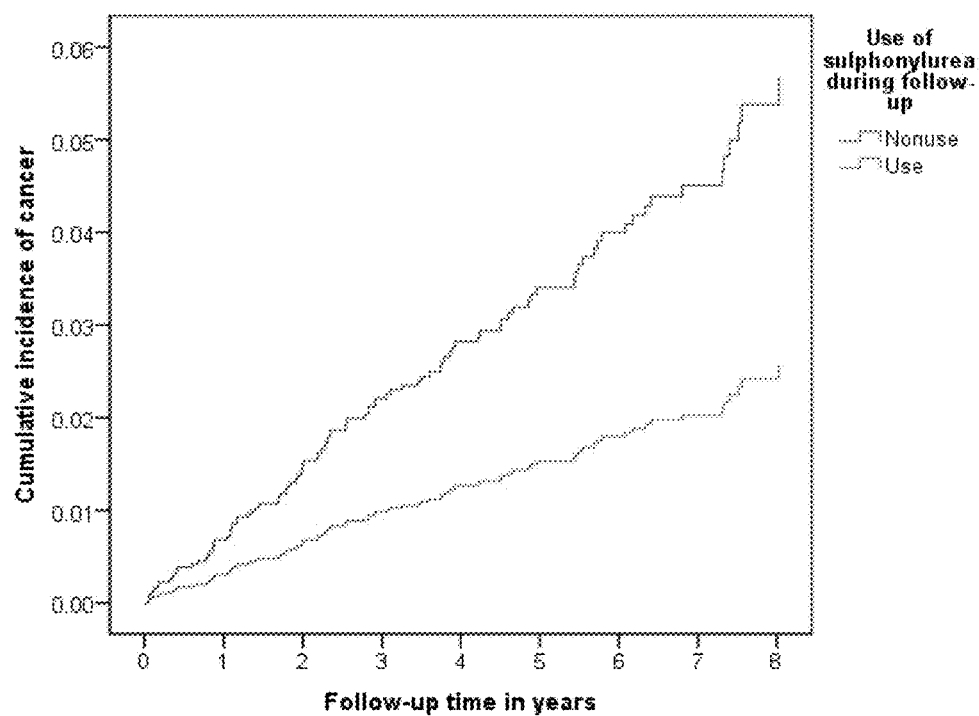

Adjusted for LDL-C related risk indicator, nonlinear associations of HDL-C and triglyceride, BMI (<24, ≥27.6 kg/m$^2$), age, sex, occupation, use of tobacco and alcohol, duration of disease, HbA1c, SBP, use of statins, ACEIs/ARBs, fibrates, insulin, metformin and TZDs during follow-up period, as well as propensity score of use of sulphonylurea during follow-up period.

Figure 19. Use of Thiazolidinedione (TZD) and cumulative incidence of cancer among patients with Type 2 diabetes who did not use TZDs within 2.5 years prior to the enrolment (prevalent users excluded). Please refer to tables 8 and 9 for patient characteristics

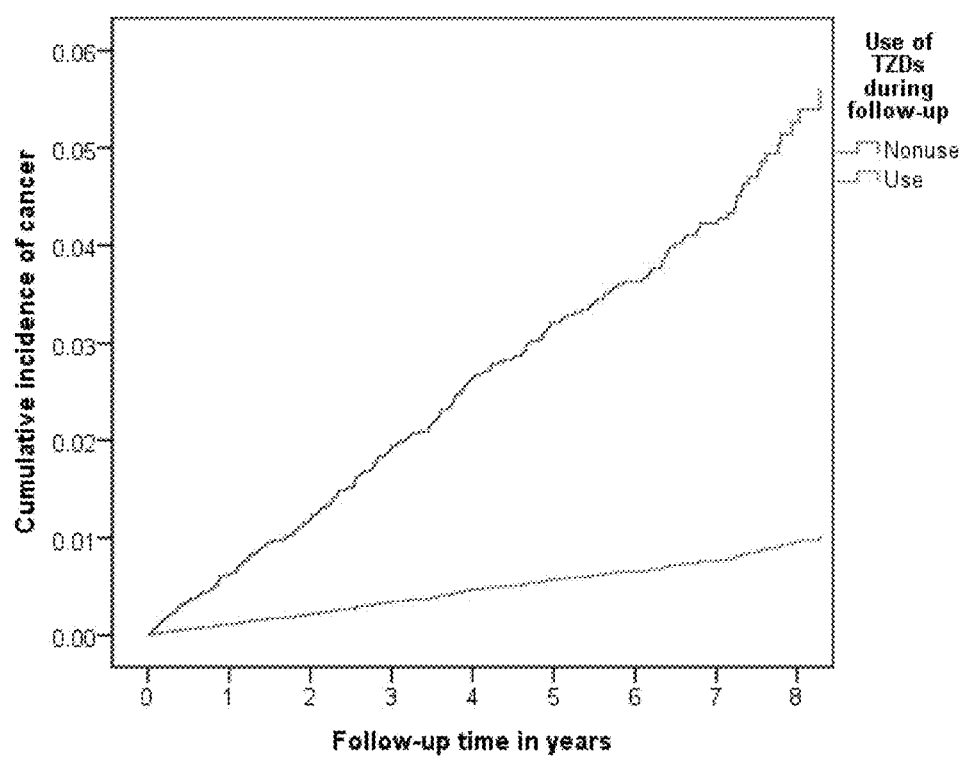

Adjusted for LDL-C related risk indicator, nonlinear associations of HDL-C and triglyceride, BMI (<24, ≥27.6 kg/m$^2$), age, sex, occupation, use of tobacco and alcohol, duration of disease, HbA1c, SBP, use of statins, ACEIs/ARB, fibrates, insulin, metformin and sulphonyluria during follow-up period, as well as propensity score of use of TZDs during follow-up period.

Figure 20. Use of statins and cumulative incidence of cancer among patients with Type 2 diabetes who did not use statins within 2.5 years prior to the enrolment (prevalent users excluded). Please refer to tables 8 and 9 for patient characteristics.

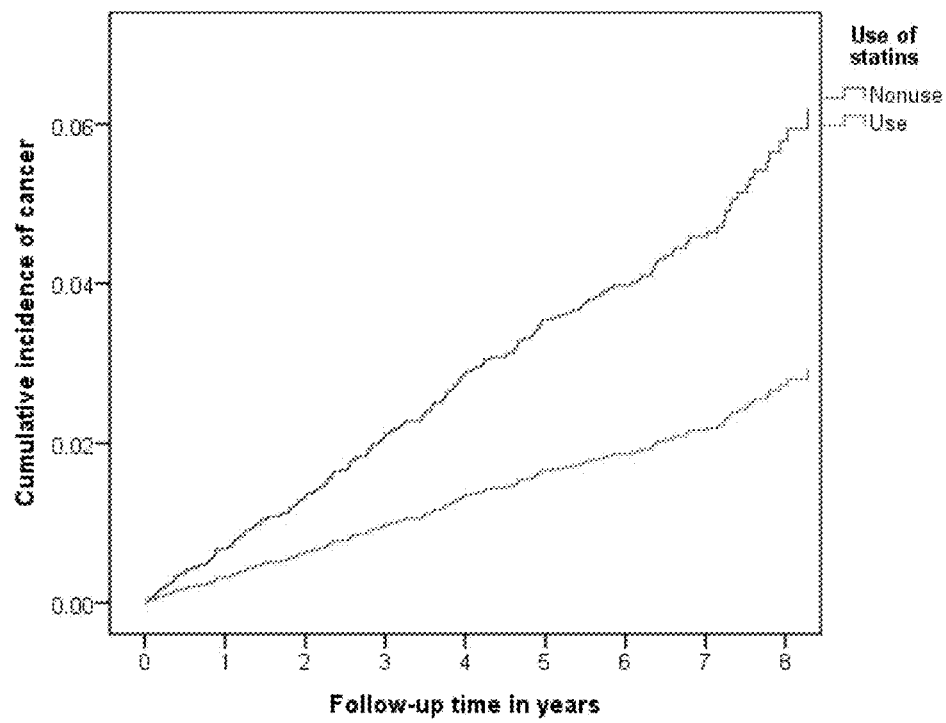

Adjusted for LDL-C related risk indicator, nonlinear associations of HDL-C and triglyceride, BMI (<24, ≥27.6 kg/m$^2$), age, sex, occupation, smoking status, use of tobacco and alcohol, duration of disease, HbA1c, SBP, use of ACEIs/ARB, fibrates, insulin, metformin and sulphonyluria during follow-up period, as well as propensity score of use of statins during follow-up period.

Figure 21. Use of angiotensin converting enzyme inhibitors (ACEIs) or angiotensin II receptor blockers (ARBs) and cumulative incidence of cancer among patients with Type 2 diabetes who did not use ACEIs and ARBs within 2.5 years prior to the enrolment (prevalent users excluded). Please refer to tables 8 and 9 for patient characteristics.

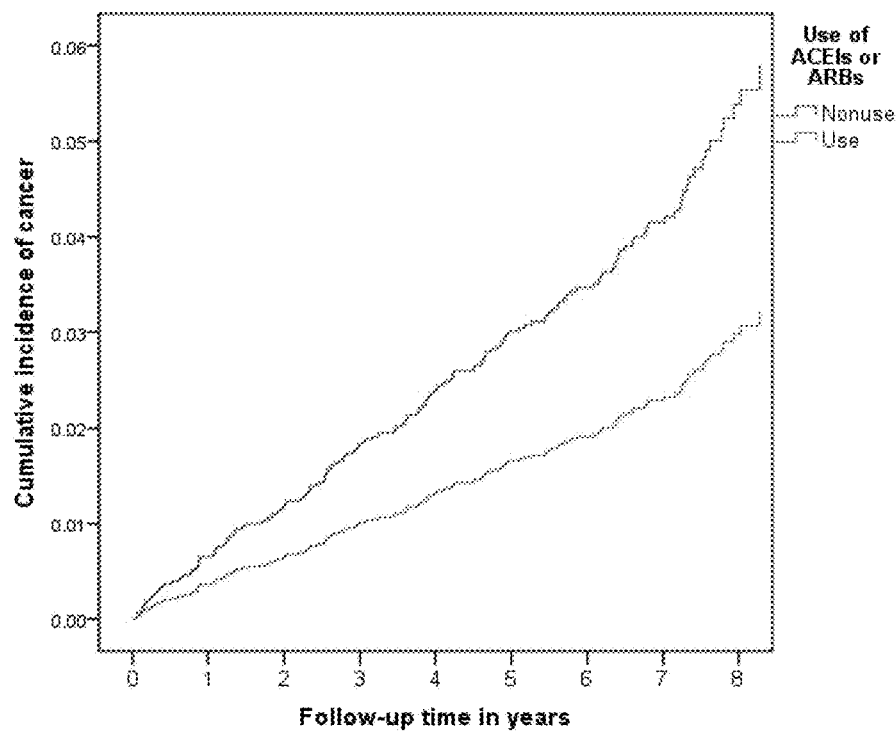

Adjusted for LDL-C related risk indicator, nonlinear associations of HDL-C and triglyceride, BMI (<24, ≥27.6 kg/m$^2$), age, sex, occupation, use of tobacco and alcohol, duration of disease, HbA1c, SBP, use of statins, fibrates, insulin, metformin and sulphonyluria during follow-up period, as well as propensity score of use of ACEIs or ARBs during follow-up period (c-statistics=0.80).

Figure 22 Number of risk factors (HbA$_{1c}$≥7.0%, non-use of statins and non-use of ACEIs or ARBs) and cumulative risk of cancer among patients with Type 2 diabetes who did not use statins, ACEIs or ARBs within 2.5 years prior to the enrolment (prevalent users excluded). Please refer to tables 8 and 9 for patient characteristics.

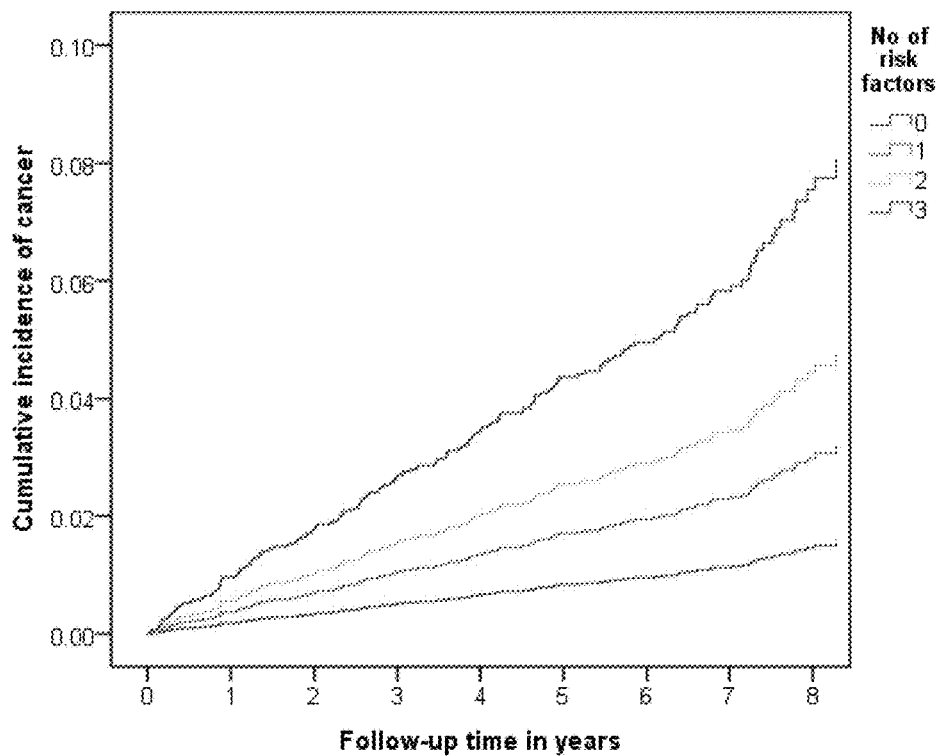

Adjusted for LDL-C related risk indicator, nonlinear associations of HDL-C and triglyceride, BMI (<24, ≥27.6 kg/m$^2$), age, sex, occupation, use of tobacco and alcohol, duration of disease, SBP, use of fibrates, insulin and oral antidiabetes drugs during follow-up period, as well as propensity scores of use of statins and ACEIs/ARBs during follow-up period. P<.001 for 3 vs. 0; for 2 vs. 0 and for 1 vs. 0

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Synthetic construct

<400> SEQUENCE: 1
taagagctcc agacctgatg aattc                                           25

<210> SEQ ID NO 2
<211> LENGTH: 26
<212> TYPE: DNA
<213> ORGANISM: Artificial Sequence
<220> FEATURE:
<223> OTHER INFORMATION: Synthetic construct

<400> SEQUENCE: 2
ctactcgagt agctgtctct ttgaac                                          26

<210> SEQ ID NO 3
<211> LENGTH: 44
<212> TYPE: DNA
<213> ORGANISM: Artificial Sequence
<220> FEATURE:
<223> OTHER INFORMATION: Synthetic construct

<400> SEQUENCE: 3
```

```
cctatgaagc cacaaacaag taatacatgt gccagtaaag ttgg              44

<210> SEQ ID NO 4
<211> LENGTH: 44
<212> TYPE: DNA
<213> ORGANISM: Artificial Sequence
<220> FEATURE:
<223> OTHER INFORMATION: Synthetic construct

<400> SEQUENCE: 4
ccaactttac tggcacatgt attacttgtt tgtggcttca tagg              44
```

BIOMARKERS FOR DIABETES

This application is the U.S. National Stage Entry of PCT/CN2013/071053, filed Jan. 28, 2013, which claims priority to U.S. Provisional Patent Application No. 61/591,598, filed Jan. 27, 2012, the contents of which are incorporated by reference in the entirety for all purposes.

REFERENCE TO A "SEQUENCE LISTING" SUBMITTED AS ASCII TEXT FILES VIA EFS-WEB

The Sequence Listing written in file 080015-009010US-0904868_SequenceListing.txt created on Feb. 22, 2017, 1,097 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Diabetes mellitus, often referred to simply as diabetes, encompasses a variety of conditions that involve disordered metabolism, the typical feature of which is abnormally high blood sugar levels (hyperglycemia). Blood sugar levels are controlled by a complex network of chemicals and hormones in the human body, including the hormone, insulin, produced by the beta cells of the pancreas. The abnormally high level of blood sugar seen in a diabetic patient is caused by defects in either insulin secretion or insulin action, attributable to a combination of hereditary, acquired, and environmental factors. Majority of diabetes are either type 1 diabetes, previously known as childhood-onset diabetes and insulin-dependent diabetes, or type 2 diabetes, previously known as adult-onset diabetes and insulin-independent diabetes.

Type 1 diabetes is characterized by loss of the insulin-producing beta cells of the islets of Langerhans in the pancreas, resulting in a deficiency of insulin production. The principal treatment for this type of diabetes is therefore delivery of artificial insulin, usually via injection. Type 2 diabetes is more common than type 1 diabetes with over 90% of affected people having type 2 diabetes. The latter is closely associated with modernization characterized by obesity and insulin resistance (reduced insulin sensitivity) although diminished insulin production is needed for development of overt hyperglycemia. Both twin and family studies support a strong genetic component for type 2 diabetes. Recent genetic implicate multiple common genetic variants in the development of type 2 diabetes although these factors only explained a small percentage of the variance of the genetic risk of type 2 diabetes. Furthermore, there is strong evidence showing inter-ethnic differences in distribution and frequency of genetic or sequence variants for diabetes such that many of these variants discovered in Caucasian populations may not be applicable to Asian population due to different patterns of linkage disequilibrium and recombination hotspots.

Various factors are known to be indicative of a person's risk to develop type 2 diabetes, most of them strongly influenced by the person's lifestyle, age, ethnic background, and family history. The presence of at least one, often more than one, of these risk factors, such as a body mass index (BMI) in the range of obesity (especially central obesity due to accumulation of excess visceral fat as indicated by large waist circumference), elevated blood glucose or insulin level (especially elevated fasting or post prandial blood glucose or insulin level), and reduced sensitivity to insulin, predisposes a person to the high likelihood of developing type 2 diabetes, if no corrective measure is taken.

As people's living standards continue to improve globally, the number of individuals suffering from diabetes is also rapidly increasing. The World Health Organization (WHO) estimates that by 2030 the number of people living with diabetes will exceed 350 million worldwide. Due to the rising incidence of diabetes, its chronic nature without an ultimate cure, and serious health implications associated with its complications, including but not limited to cardiovascular disease, kidney failure, cancer, blindness, leg amputation, there exists an urgent need for new and effective means to assess or predict the risk of individuals who might later develop diabetic conditions, so that prophylactic measures can be taken to prevent or delay the onset of diabetes in these individuals or to reduce severity of the pertinent symptoms/risks associated with diabetes.

It is now clear that diabetes increases risk of all site cancers by 30% except for prostatic cancer. In the US, Asian subjects are known to have higher cancer risk than non-Asian subjects, in particular, liver and gastric cancers. These predilections for cancer development may be related to the interaction between external carcinogens (e.g., tobacco, alcohol, food, and low grade infections, such as hepatitis B infection) and abnormal metabolic environment due to high blood glucose, high blood lipid, and kidney failure. Besides, subjects with chronic kidney disease are at extremely high risk for cardiovascular disease due to changes in metabolic milieu including oxidative stress, low grade inflammation, vascular calcification, and anemia, which will increase risk of vascular damage. Thus, a person with diabetes or at risk for diabetes has very high risk for these co-morbidities including but not limited to cancer, cardiovascular and kidney disease, which are closely linked.

There are also clinical and experimental data showing that good glycemic control and use of certain drugs such as statins (which inhibit the HMG coA reductase), blockers of renin angiotensin system, and blood glucose lowering drugs including but not limited to insulin, sulphonylureas, metformin and glitazones, may not only reduce the risk of cardiovascular and renal disease but also cancer. These preventive measures are especially important in high risk subjects such as those who have additional risk factors for cancer and cardiovascular disease, e.g., positive family history of diabetes (suggesting the possibility of harboring other genetic factors yet to be identified), chronic hepatitis B infection, chronic kidney disease, and low BMI (reflecting poor pancreatic beta cell functions). In these high risk subjects, detection of genetic risk factors before severe metabolic decompensation will help clinicians to intensify treatment in order to prevent metabolic deterioration and optimize metabolic control to reduce risk of cancer, cardiovascular and renal disease.

Because of the enormous social and economical impact the above discussed diseases incurs globally, there exist clear and immediate needs to develop new and effective means for accurate diagnosis of these diseases or early assessment a patient's risk of developing these diseases in the future, such that early intervention may be performed to minimize the harmful effects associated with these diseases and/or the risk of developing the diseases. The present invention fulfills this and other related needs.

BRIEF SUMMARY OF THE INVENTION

In one aspect, the present invention provides a method for assessing the presence or risk of type 2 diabetes, cancer, or cardiovascular disease in a subject. The method includes the steps of: (a) performing an assay that determines nucleotide sequence of at least a portion of genomic sequence of carboxypeptidase E (CPE) present in a biological sample taken from the subject, and (b) comparing the sequence determined in step (a) with a corresponding standard sequence of CPE. When a variation in the sequence determined in step (a) is detected when compared with the standard sequence, it indicates that the subject has or is at risk of developing type 2 diabetes, cancer, or cardiovascular disease.

In some cases, the sample is a blood or saliva sample. In other cases, the subject is an Asian descent. In some cases, the subject has a BMI no greater than 25 kg/m$^2$. In other cases, the subject has a family history of type 2 diabetes, cancer, or cardiovascular disease but has not been diagnosed of type 2 diabetes, cancer, or cardiovascular disease.

In some embodiments, the assay in step (a) includes an amplification reaction, such as a polymerase chain reaction (PCR). In other embodiments, the assay in step (a) includes mass spectrometry. Any conventional or more advanced polynucleotide sequencing or genotyping analysis can be used in this step. In some examples, when the subject is indicated as having or at risk of developing type 2 diabetes, cancer, or cardiovascular disease, the method may further include the step of administering to the subject a cholesterol lowering drug or a blood glucose lowering drug. In other examples, the method may further involve repeating steps (a) and (b) with insulin degrading enzyme (IDE). In other words, instead of the CPE genomic sequence, the IDE genomic sequence is analyzed in the same fashion as described in steps (a) and (b). When a variation in the IDE genomic sequence obtained in the sample is detected when compared with the corresponding standard sequence, it indicates that the subject has or is at risk of developing type 2 diabetes, cancer, or cardiovascular disease.

In another aspect, the present invention provides a method for assessing the presence or risk of type 2 diabetes, cancer, or cardiovascular disease in a subject. The method comprises the steps of: (a) performing an assay that determines nucleotide sequence of at least a portion of genomic sequence of insulin degrading enzyme (IDE) present in a biological sample taken from the subject, and (b) comparing the sequence determined in step (a) with a corresponding standard sequence of IDE. When a variation in the sequence determined in step (a) is detected when compared with the standard sequence, the variation indicates that the subject has or is at risk of developing type 2 diabetes, cancer, or cardiovascular disease.

In some cases, the sample is a blood or saliva sample. In other cases, the subject is an Asian descent. In some cases, the subject has a BMI no greater than 25 kg/m$^2$. In other cases, the subject has a family history of type 2 diabetes, cancer, or cardiovascular disease but has not been diagnosed of type 2 diabetes, cancer, or cardiovascular disease. In some examples, the assay in step (a) includes an amplification reaction, such as a polymerase chain reaction (PCR). In other examples, the assay in step (a) includes mass spectrometry. Any conventional or more advanced sequencing or genotyping analysis can be used in this step.

In some embodiments of the claimed method, when the subject is indicated as having or at risk of developing type 2 diabetes, cancer, or cardiovascular disease, the method further includes the step of administering to the subject a cholesterol lowering drug or a blood glucose lowering drug. In some embodiments, the method may further involve repeating steps (a) and (b) with carboxypeptidase E (CPE), when a variation in the CPE genomic sequence in the sample is detected when compared with the corresponding standard sequence, indicating that the subject has or is at risk of developing type 2 diabetes, cancer, or cardiovascular disease. One exemplary sequence variation is polymorphism rs1583645 for CPE or rs6583813 for IDE. In some cases, the claimed method may further involve repeating steps (a) and (b) with one or more of genes such as LIPC, LPL, CETP, PPARG, GNB3, NOS3, LTA, AGTA1, ADRB2, ADRB3, NPPA, ADD1, SCNN1A, MMP3, ALR2, TNF, APOE, and APOC3. When a variation in the genomic sequence determined in the sample is detected when compared with the corresponding standard sequence, it indicates that the subject has or is at risk of developing type 2 diabetes, cancer, or cardiovascular disease.

In yet another aspect, the present invention provides a kit for assessing the presence or risk of type 2 diabetes, cancer, or cardiovascular disease in a subject. The kit comprises two oligonucleotide primers that are useful for specifically amplifying either (1) at least a segment of genomic sequence of carboxypeptidase E (CPE) or insulin degradation enzyme (IDE); or (2) complement of (1), in an amplification reaction. In some cases, the amplification reaction is a polymerase chain reaction (PCR). In some cases, the kit comprises two sets of oligonucleotide primers, one for specifically amplifying at least a segment of the CPE genomic sequence and the other for specifically amplifying at least a segment of the IDE genomic sequence. Typically, the kit includes an instruction manual that provides directions for users to practice the amplification reaction and to assess the presence or risk of type 2 diabetes, cancer, or cardiovascular disease in a subject.

In yet another aspect, the present invention provides an array for assessing the presence or risk of type 2 diabetes, cancer, or cardiovascular disease in a subject. Typically, the array is an oligonucleotide array, comprising one or more oligonucleotide probes for specifically detecting: (1) at least a segment of genomic sequence of carboxypeptidase E (CPE) or insulin degradation enzyme (IDE); or (2) complement of (1). The array may comprise a solid substrate onto which the oligonucleotide(s) have been immobilized. In some cases, the array comprises at least two oligonucleotides, one for specific detection of a segment of the CPE genomic sequence or its complement and the other for specific detection of a segment of the IDE genomic sequence or its complement. Optionally, the array includes additional oligonucleotides, which are for specific detection of at least a segment of one or more genomic sequences such as such as LIPC, LPL, CETP, PPARG, GNB3, NOS3, LTA, AGTA1, ADRB2, ADRB3, NPPA, ADD1, SCNN1A, MMP3, ALR2, TNF, APOE, and APOC3. In some cases, specific detection of a genomic sequence (or its complement) involves polynucleotide sequence specific hybridization between an oligonucleotide probe and its target sequence based on Watson-Crick base pairing.

BRIEF DESCRIPTION OF THE DRAWINGS

FIG. 1 illustrates how certain genomic sequence variations may contribute to increased risk of type 2 diabetes, cancer, and cardiovascular disease and the use of genetic variants to identify high risk subjects for early intervention.

FIG. 2 Association of type 2 diabetes with a genetic risk score derived from risk alleles of rs1583645 of CPE and rs6583813 of IDE genes in all Asian subjects analyzed by logistic regression analysis with adjustment for "Study Population" encoding various cohorts from Hong Kong Chinese, Shanghai Chinese, Japanese and Korean.

FIG. 3 Associations of genetic risk scores derived from risk alleles of rs1583645 of CPE and rs6583813 of IDE genes with (A) plasma islet amyloid polypeptide (IAPP) and (B) molar ratio of IAPP to insulin (IAPP/INS) in 85 unrelated non-diabetic controls selected from a family-based cohort.

FIG. 4 Overall hypothesis depicting the possible pathogenetic roles of dysregulation of human islet amyloid polypeptide pathways in causing beta cell dysfunction at various stages including maturation, degradation, oligomerization and stabilization.

FIG. 5 Gene structure within the proximity of CPE rs1583645 A/G polymorphism and functional studies of these genetic variants using the luciferase activity assays.

FIG. 6 Kaplan Miere curve showing the risk associations of all-site cancers with genetic variants of IDE in type 2 diabetic patients with positive family history after adjustment for confounding variables.

FIG. 7 Kaplan Miere curve showing the risk associations of cardiovascular disease with genetic variants of CPE in non-obese type 2 diabetic patients after adjustment for confounding variables.

FIG. 8 Kaplan Miere curve showing the risk associations of cancer with genetic risk scores of CPE and IDE in type 2 diabetic patients with positive family history after adjustment for confounding variables.

FIGS. 9-12 Structural equation models showing the genotype-phenotype interactions which explain large variance of renal function in type 2 diabetes attributable to obesity, blood pressure, lipid and glucose control and their genetic determinants FIG. 13 Structural equation models showing the causal relationships between chronic kidney disease and cardiovascular disease and the large variance explained by age of diagnosis, chronic hepatitis B infection, renal function, blood pressure, blood glucose and blood lipids.

FIG. 14 Risk associations of cancer risk and $HbA_{1c}$ in epidemiological studies and metaanalysis supporting the possible causal role of hyperglycemia and cancer risk.

FIG. 15 Cumulative incidence of all-site cancers in a 10-year prospective cohort of 4200 Chinese type 2 diabetes stratified by chronic hepatitis B viral (HBV) infection status and $HbA_{1c} \geq 7.4\%$.

FIG. 16 Use of insulin and cumulative incidence of cancer among patients with Type 2 diabetes who did not use insulin within 2.5 years prior to the enrolment (prevalent users excluded) adjusted for propensity score (drug indications), risk factors and use of other medications (also refer to tables 8 and 9 for patient characteristics).

FIG. 17 Use of metformin and cumulative incidence of cancer among patients with Type 2 diabetes who did not use metformin within 2.5 years prior to the enrolment (prevalent users excluded) adjusted for propensity score (drug indications), risk factors and use of other medications (also refer to tables 8 and 9 for patient characteristics).

FIG. 18 Use of sulphonylurea and cumulative incidence of cancer among patients with Type 2 diabetes who did not use sulphonylurea within 2.5 years prior to the enrolment (prevalent users excluded) adjusted for propensity score (drug indications), risk factors and use of other medications (also refer to tables 8 and 9 for patient characteristics).

FIG. 19 Use of Thiazolidinedione (TZD) and cumulative incidence of cancer among patients with Type 2 diabetes who did not use TZDs within 2.5 years prior to the enrolment (prevalent users excluded) adjusted for propensity score (drug indications), risk factors and use of other medications (also refer to tables 8 and 9 for patient characteristics).

FIG. 20 Use of statins and cumulative incidence of cancer among patients with Type 2 diabetes who did not use statins within 2.5 years prior to the enrolment (prevalent users excluded) adjusted for propensity score (drug indications), risk factors and use of other medications.

FIG. 21 Use of angiotensin converting enzyme inhibitors (ACEIs) or angiotensin II receptor blockers (ARBs) and cumulative incidence of cancer among patients with Type 2 diabetes who did not use ACEIs and ARBs within 2.5 years prior to the enrolment (prevalent users excluded) adjusted for propensity score (drug indications), risk factors and use of other medications (also refer to tables 8 and 9 for patient characteristics).

FIG. 22 Number of risk factors ($HbA_{1c} \geq 7.0\%$, non-use of statins and non-use of ACEIs or ARBs) and cumulative risk of cancer among patients with Type 2 diabetes who did not use statins, ACEIs or ARBs within 2.5 years prior to the enrolment (prevalent users excluded) adjusted for propensity score (drug indications), risk factors and use of other medications (also refer to tables 8 and 9 for patient characteristics).

DEFINITIONS

The term "type 2 diabetes" refers to a metabolic disorder that is characterized by high blood glucose in the context of insulin resistance and relative insulin deficiency. Type 2 diabetes may be caused by a combination of lifestyle and genetic factors. Risk factors include but not limited to obesity, hypertension, high blood cholesterol, metabolic syndrome (high triglyceride, low HDL-C, high blood glucose, high blood pressure, large waist), endocrine disorders (e.g., Cushing's syndrome), chronic pancreatitis, use of certain drugs, aging, energy dense diets (e.g., high-fat and high glucose), and an inactive lifestyle. On the other hand, having relatives (especially first degree) with type 2 increases risks of developing type 2 diabetes substantially. Symptoms of type 2 diabetes often include polyuria (frequent urination), polydipsia (increased thirst), polyphagia (increased hunger), fatigue, and weight loss. Co-morbidities associated with type 2 diabetes due to high blood sugar and abnormal metabolic milieu (e.g., low grade inflammation, oxidative stress and abnormal lipids) include increased risk of heart attacks, strokes, limb amputation, visual loss, kidney failure, cancers, and cognitive impairment.

The term "cancer" is used in this application to broadly refer to any disease in which a group of cells display uncontrolled growth, invasion that intrudes upon and destroys adjacent tissues, and often metastasizes, wherein these cells of uncontrolled growth spread to other locations in the body via the lymphatic system or through the bloodstream. Unless specified, a "cancer" may occur at any anatomic site within a patient's body. Cancer cells are typically those with three malignant properties that differentiate malignant tumors (or cancers) from benign tumors: cancer cells grow uncontrollably, directly invade locally, or metastasize to regional lymph nodes or distant body sites like brain, bone, liver, or other organs.

The term "cardiovascular disease" refers to a broad class of diseases that involve the heart or blood vessels (arteries and veins) and affect the cardiovascular system, such as conditions related to atherosclerosis (arterial disease). These include but not limited to stroke, coronary heart disease and peripheral vascular disease. Known risk factors for cardiovascular diseases include unhealthy eating, lack of exercise, obesity, improperly managed diabetes, abnormal blood lipids, high blood pressure, consumption of alcohol and/or tobacco, as well as genetic background.

As used herein, the term "body mass index" or "BMI" refers to a number calculated from a person's weight and height to reflect the "fatness" or "thinness" of a person. More specifically, BMI=mass (kg)/(height (m))$^2$ or mass (lb)×703/(height (in))$^2$. Typically, in Caucasian populations, a BMI of 20 to 25 kg/m$^2$ is considered optimal weight; a BMI lower than 20 kg/m$^2$ suggests the person is underweight whereas a BMI above 25 kg/m$^2$ may indicate the person is overweight; a BMI above 30 kg/m$^2$ suggests the person is obese; and a BMI over 40 kg/m$^2$ indicates the person to be morbidly obese. Compared to Caucasians, Asians have more body fat for the same degree of BMI and waist circumference. Thus, normal weight and obesity in Asians are defined as <23 kg/m$^2$ and ≤25 kg/m$^2$ respectively. While high BMI may predict risk for diabetes or prediabetes, people with low BMI, which correlates with beta cell function, are also at high risk, especially if these subjects develop central obesity, which tends to be associated with insulin resistance or reduced insulin sensitivity.

In this disclosure the term "biological sample" or "sample" includes any section of tissue or bodily fluid taken from a test subject such as a biopsy and autopsy sample, and frozen section taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure, the term "biopsy" refers to the process of removing a tissue sample for diagnostic or prognostic evaluation, and to the tissue specimen itself. Any biopsy technique known in the art can be applied to the methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise endoscopy such as colonoscopy. A wide range of biopsy techniques are well known to those skilled in the art who will choose between them and implement them with minimal experimentation.

In this disclosure, the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by a polymerase chain reaction or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription and/or translation of the gene product and the regulation of the transcription and/or translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refer to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human carboxypeptidase E (CPE) or insulin degrading enzyme (IDE) gene or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. In this disclosure the term "primer pair" means a pair of primers that hybridize to opposite strands a target DNA molecule or to regions of the target DNA which flank a nucleotide sequence to be amplified. In this disclosure the term "primer site," means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

A "standard sequence" as used herein refers to the polynucleotide sequence of a predetermined genomic DNA segment, e.g., a defined portion or the entire length of a human genomic sequence of a given gene, such as the human carboxypeptidase E (CPE) or insulin degrading enzyme (IDE) genomic sequence, including 2 kb upstream and 2 kb downstream flanking sequences, that is present in a publically accessible database, e.g., the University of California Santa Cruz database (hg18), as the standard human genomic sequence for that particular gene. When a genomic DNA sequence determined from a test sample is compared with a "standard sequence," the test sequence is aligned with the "standard sequence" at the corresponding nucleotide bases of the genomic sequence to reveal any sequence variation.

The standard genomic sequence for human carboxypeptidase E (CPE) gene is provided as Chromosome 4:166,298,097-166,421,482 The standard sequence for human insulin degrading enzyme (IDE) gene is provided as Chromosome 10: 94,209,441-94,259,518.

The term "amount" as used in this application refers to the quantity of a polynucleotide of interest or a polypeptide of interest present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "effective amount" as used herein refers to an amount of a given substance that is sufficient in quantity to produce a desired effect. For example, an effective amount of a cholesterol lowering drug or a blood glucose lowering drug is the amount of said drug to achieve a decreased level of cholesterol or blood glucose, respectively, in a patient who has been given the drug for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, type 2 diabetes, cancer, or cardiovascular disease. Subjects also include individuals currently undergoing therapy that seek manipulation of the therapeutic regimen. Subjects or individuals in need of treatment include those that demonstrate symptoms of type 2 diabetes, cancer, or cardiovascular disease, or are at risk of suffering from type 2 diabetes, cancer, or cardiovascular disease or related symptoms. For example, a subject in need of treatment includes individuals with a genetic predisposition or family history for type 2 diabetes, cancer, or cardiovascular disease, those that have suffered relevant symptoms in the past, those that have been exposed to a triggering substance or event, as well as those suffering from chronic or acute symptoms of the condition. A "subject in need of treatment" may be at any age of life.

DETAILED DESCRIPTION OF THE INVENTION

I. Introduction

The present inventors discovered for the first time the correlation between genomic sequence variation in one or more of certain genes such as the carboxypeptidase E (CPE) and insulin degrading enzyme (IDE) genes and medical conditions such as type 2 diabetes, cancer, and cardiovascular disease in human subjects. This discovery allows medical professionals to diagnose type 2 diabetes, cancer, and cardiovascular disease in a patient or assess the risk of developing type 2 diabetes, cancer, and cardiovascular disease in a subject at risk by studying the subject's genomic sequence of a relevant gene and then comparing the subject's sequence with a standard genomic sequence that has been determined as a part of the standard human genome. Detection of such sequence variation(s) indicates the presence or elevated risk of developing type 2 diabetes, cancer, or cardiovascular disease in the subject. The detection of pertinent genomic sequence variation(s) can further guide physicians to devise or modify treatment plans for a subject in both prevention and therapeutic measures.

The present inventors have quantified the complex interrelationship between cardiovascular disease and chronic kidney disease as well as interactions amongst multiple genetic variants, which explain large variance of phenotypes including obesity, blood pressure, blood lipids, and blood glucose. The consequent genotype-phenotype interactions also explain a large variance of the renal function, which influences risk of cardiovascular disease.

The present inventors have discovered for the first time the interactions between suboptimal glycemic control defined as glycated hemoglobin 7% and chronic hepatitis B infection on risk of cancer, notably hepatocellular cancer. They have also discovered the marked benefits of use of blood glucose lowering drugs and the benefits of attaining glycemic control and use of statins and blockers or renin angiotensin system on cancer risks.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human CPE or IDE gene, and synthetic oligonucleotides (e.g., primers) can be verified using, e.g., the chain termination method for sequencing double-stranded templates of Wallace et al., *Gene* 16: 21-26 (1981).

III. Acquisition of Biological Samples and Analysis of Genomic DNA Sequence

The present invention relates to determining at least a portion of the genomic sequence of a pertinent gene, such as the human CPE or IDE gene, found in a biological sample taken from a person being tested, as a means to detect the presence and/or to assess the risk of developing type 2 diabetes, cancer, or cardiovascular disease in that person. Thus, the first steps of practicing this invention are to obtain a biological sample (e.g., tissue or bodily fluid sample) from a test subject and extract genomic DNA from the sample.

A. Acquisition and Preparation of Samples

A biological sample is obtained from a person to be tested or assessed for risk of developing type 2 diabetes, cancer, or cardiovascular disease using a method of the present invention. Collection of a tissue or fluid sample from an individual is performed in accordance with the standard protocol laboratories, hospitals or clinics generally follow, such as during a biopsy, blood drawing, saliva collection, or oral swab. An appropriate amount of sample is collected and may be stored according to standard procedures prior to further preparation.

The analysis of genomic DNA found in a subject's sample according to the present invention may be performed using essentially any tissue or bodily fluid, so long as genomic DNA is expected to be present in such sample. The methods for preparing tissue or fluid samples for nucleic acid extraction are well known among those of skill in the art. For example, a subject's epithelial tissue sample should be first treated to disrupt cellular membrane so as to release nucleic acids contained within the cells.

B. Determination of Genomic Sequence

Possible sequence variation within a segment of a pertinent gene (such as the CPE or IDE gene) is investigated to provide indication as to whether a test subject is suffering from type 2 diabetes, cancer, and/or cardiovascular disease, or whether the subject is at risk of developing type 2 diabetes, cancer, and/or cardiovascular disease in the future.

Typically a segment of the genomic sequence of an appropriate length is selected for sequencing analysis. The segment may be chosen from the genomic sequence of a pertinent gene defined by the same boundaries defining the gene's cDNA sequence, plus about 2,000 base pairs upstream and downstream from the boundaries. The length of the genomic sequence being analyzed is usually at least 15 or 20 contiguous nucleotides, and may be longer with at least 25, 30, 50, 100, 200, 300, 400, or more contiguous nucleotides.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. Optionally, other components (such as proteins and lipids) may be removed from the biological sample prior to further analysis of the genomic DNA.

2. Optional Amplification and Sequence Analysis

Following the desired processing of DNA in a biological sample, the DNA is then subjected to sequence-based analysis, such that the genomic sequence of one or more of the pertinent genes found in a test subject may be determined and then compared with a standard sequence to detect any possible sequence variation. An amplification reaction is optional prior to the sequence analysis. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for determining the polynucleotide sequence of a genomic DNA for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Corresponding Standard Sequence

In order to practice the method of this invention, the standard genomic sequence(s) for one or more pertinent genes, such as CPE, IDE, LIPC, LPL, CETP, PPARG, GNB3, NOS3, LTA, AGTA1, ADRB2, ADRB3, NPPA, ADD1, SCNN1A, MMP3, ALR2, TNF, APOE, and APOC3 genes, will be chosen before the comparison with a test subject's genomic sequence of the corresponding gene at the corresponding location may be performed. Table 7 provides the full names and genomic sequences for these genes.

V. Treatment and Prevention

By illustrating the correlation between genomic sequence variation in one or more of the specific genes named above and the presence or heightened risk of developing type 2 diabetes, cancers, or cardiovascular diseases among subjects having such variation, especially those fitting certain profiles, such as those of Asian descent and/or with a BMI no greater than 25 $kg/m^2$, the present inventors have provided a valuable tool for clinicians to determine, often in combination with other information and diagnostic or predictive or screening test results, how a subject having certain genomic sequence variation(s) should be monitored and/or treated for type 2 diabetes, cancer of any site, and/or cardiovascular disease such that the symptoms of these conditions may be prevented, eliminated, ameliorated, reduced in severity and/or frequency, or delayed in their onset. For example, a physician may prescribe both pharmacological and non-pharmacological treatments such as lifestyle modification (e.g., reduce body weight by 5%, high fibre diet, walking for at least 150 minutes weekly) and medicines known to reduce risk of onset of diabetes (e.g., metformin, alpha glucosidase inhibitors, lipase inhibitors) to a subject who has been deemed by the method of the present invention to have an elevated risk of developing type 2 diabetes. A subject is deemed to have elevated risk of developing cancer of all sites may be subject to frequent screening for various types of cancer, such that the subject's chance of survival will be enhanced by way of early detection and therefore timely and effective treatment including optimal glycemic control using blood glucose lowering drugs and medications which can block the adverse effects of hyperglycemia, such as statins and blockers of renin angiotensin system. For a subject who has been deemed by the method of the present invention to suffer from or at risk of developing cardiovascular disease, the attending physician may prescribe medications that will counter known risk factors of cardiovascular disease such as high levels of blood cholesterol and triglycerol, as well as place the subject under regular testing and monitoring of coronary artery condition.

VI. Kits and Devices

The present invention provides compositions and kits for practicing the methods described herein to detect possible genomic sequence variation of certain gene(s) in a subject, which can be used for various purposes such as detecting or diagnosing the presence of type 2 diabetes, cancer, and/or cardiovascular disease in a subject, determining the risk of developing type 2 diabetes, cancer, and cardiovascular disease in a subject, and guiding the treatment plan for these conditions in the subject.

Kits for carrying out assays for determining the nucleotide sequence of a relevant genomic sequence typically include at least one oligonucleotide useful for specific hybridization with a predetermined segment of a pertinent genomic sequence. Optionally, this oligonucleotide is labeled with a detectable moiety. In some cases, the oligonucleotide specifically hybridizes with the standard sequence only but not with any of the variant sequences. In other cases, the oligonucleotide specifically hybridizes with one particular version of the variant sequence but not with other versions, nor with the standard sequence.

In some cases, the kits may include at least two oligonucleotide primers that can be used in the amplification of at least one segment of the genomic sequence of one pertinent gene (such as the CPE or IDE gene) by PCR. In some examples, at least one of the oligonucleotide primers is designed to anneal only to the standard sequence or only to a particular version of the variant sequences.

In addition, the kits of this invention may provide instruction manuals to guide users in analyzing test samples and assessing the presence or future risk of type 2 diabetes, cancer, or cardiovascular disease in a test subject.

Furthermore, the present invention can also be embodied in a device or a system comprising one or more such devices, which is capable of carrying out all or some of the method steps described herein. For instance, in some cases, the device or system performs the following steps upon receiving a biological sample taken from a subject being tested for detecting type 2 diabetes, cancer, or cardiovascular disease, assessing the risk of developing type 2 diabetes, cancer, or cardiovascular disease, or guiding treatment of a subject having or at risk of developing any one of these conditions: (a) determining in the sample the nucleotide sequence of a pertinent genomic DNA segment; (b) comparing the sequence determined from the sample with a corresponding standard sequence; and (c) providing an output indicating whether type 2 diabetes, cancer, or cardiovascular disease is present in the subject or whether the subject is at risk of developing type 2 diabetes, cancer, or cardiovascular disease. In other cases, the device or system of the invention performs the task of steps (b) and (c), after step (a) has been performed and the genomic sequence determined from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Example 1

Objective: Over 40% of autopsy cases of type 2 diabetes (T2D) showed islet amyloid. Amylin or islet amyloid polypeptide (IAPP) is highly conserved and cosecreted with insulin. Accumulation of IAPP or its precursor, pro-IAPP, due to dysregulation in processing, degradation and stabilization can cause excessive oligomerization with beta-cell toxicity.

Research Design and Methods: 89 tag single nucleotide polymorphisms (SNPs) were screened in 6 candidate genes implicated in IAPP metabolism with replication of positive signals in a multi-centre Asian case-control cohort (N=9, 901) and the Hong Kong familial diabetes cohort (N=472). Functional analysis of significant SNPs was also performed with potential regulatory roles.

Results: In the meta-analysis, rs1583645 in the carboxypeptidase E (CPE) gene and rs6583813 in the insulin degrading enzyme (IDE) gene were associated with 1.16 (1.06-1.26) [OR:odds ratio (95% CI), $P_{meta}$=0.00] and 1.35 (1.01-1.81) ($P_{meta}$=0.045) fold increased risk of T2D. Using a genetic risk score (GRS) with each risk variant scoring 1, subjects with GRS≥3 (8.2% of the cohort) had 45% increased risk of T2D compared to those with GRS<1. In the control subjects, plasma IAPP increased and beta-cell function index declined with GRS (P=0.008 and 0.03 respectively). Luciferase activity assays showed differential transcriptional activity between rs1583645 variants in different cell lines (P<0.001 and 0.005 respectively). Bioinformatics analysis of CPE rs1583645 revealed regulatory elements for chromatin modification and allele-specific binding sites for transcription factors (TFs) while IDE rs6583813 is located within active regulatory elements for islet cells.

Conclusions: These results strongly support the importance of dysregulation of IAPP metabolism in T2D in Asian populations.

Introduction

Type 2 diabetes (T2D) is characterized by perturbation of multiple pathways with beta-cell dysfunction. Large scale genome-wide association studies (GWAS) have discovered over 40 loci associated with T2D (Voight et al., *Nat Genet* 42:579-589, 2010). In Asia, while some of these risk variants conferred 1.1-1.5 fold increased risk; this could increase to 2-3 folds in carriers with multiple genetic variants (Ng et al., *Diabetes* 57:2226-2233, 2008). Amylin or islet amyloid polypeptide (IAPP) is highly conserved and cosecreted with insulin with an enhancing effect on satiety. Over 40% of T2D autopsy cases had islet amyloid suggesting an important pathogenetic role of IAPP metabolism (Zhao et al., *Diabetes* 52:2759-66, 2003). Recent studies suggest accumulation of IAPP or its precursor, pro-IAPP, could lead to excessive oligomerization with beta-cell dysfunction (Hoppener et al., *N Engl J Med* 343:411-419, 2000) due to endoplasmic reticulum (ER) stress (Gu et al., *Life Sci* 87:724-32, 2011).

In this light, multiple enzymes are implicated in IAPP metabolism including the processing enzymes of prohormone convertase 1 and 2 (PCSK1 and PCSK2) and carboxypeptidase E (CPE) which convert pro-IAPP to IAPP; insulin degrading enzyme (IDE) which degrades IAPP and; serum amyloid P component (APCS) which stabilizes amyloid (Pepys et al., *Nature* 417:254-259, 2002; Marzban et al., *Endocrinology* 146:1808-1817, 2005; Bennett et al., *Diabetes* 52:2315-2320, 2003). There are genetic associations of risk variants of these components with T2D (Martin et al., *Diabetes* 51:3568-3572, 2002; Harrap et al., *Hum Genet* 119:541-546, 2006; Leak et al., *Mol Genet Metab* 92:145-150, 2007; Zeggini et al., *Methods Mol Biol* 376:235-250, 2007) although results are not always consistent (Sakagashira et al., *Diabetes* 45:1279-1281, 1996; Utsunomiya et al., *Diabetologia* 41:701-705, 1998; Groves et al., *Diabetes* 52:1300-1305, 2003), possibly due to insufficient samples, population heterogeneity and incomplete interrogation of gene structure.

In this report, a tag single nucleotide polymorphism (SNP) approach was used to select genetic variants of 6 candidate genes (APCS, CPE, IAPP, IDE, PCSK1 and PCSK2) implicated in IAPP metabolism (FIG. 5) and tested their independent and joint effects on risk of T2D and beta-cell function in a multi-staged experiment of Asian subjects (Table 1-3 and FIG. 2-3). The transcriptional activity of risk variants was tested (FIG. 4) and bioinformatics was used to explore their functional significance including regulatory components for chromatin structure and prediction of transcription factor binding sites (TFBSs) (Table 5).

Materials and Methods

A two-stage study was conducted including subjects of Asian ancestry recruited from Hong Kong, China, Japan, and Korea.

Recruitment of Samples

Stage-1 Study

All subjects were Han Chinese living in Hong Kong without any known ancestors of other ethnic origins. Since 1995, 30-40 diabetic patients per week underwent comprehensive assessment at the Chinese University of Hong Kong—Prince of Wales Hospital Diabetes and Endocrine Centre (CUHK-PWH-DMEC) as part of a quality improvement program. All subjects underwent detailed phenotyping to form the Hong Kong Diabetes Registry (Yang et al., Diabetes Care 30:65-70, 2007). In the stage-1 study, 459 young-onset T2D subjects were selected (defined as age of diagnosis ≤40 years with at least one affected first degree relative from the Registry). Patients with clinical or autoimmune T1D, defined as history of ketoacidosis or continuous requirement of insulin within 1 year of diagnosis with or without autoimmune antibodies, were excluded. Another 419 control subjects with normal glucose tolerance defined as fasting plasma glucose (PG)<6.1 mmol/L and no family history of diabetes were recruited from a community-based health screening program and hospital volunteers (Liu et al., Diabetes Care 29:379-384, 2006).

Stage-2 Study

Included in this stage-2 study were: 1) a random unrelated case-control cohort comprising 3,092 Hong Kong Chinese, 3,388 Chinese from Shanghai, 1,393 Koreans and 1,150 Japanese and 2) 472 related subjects recruited from Hong Kong for analysis using Family-Based Association Test (FBAT). All subjects were recruited as part of a diabetes gene discovery program in the respective countries with previously described (Ng et al., Diabetes 57:2226-2233, 2008; Ng et al., Diabetes 53:1609-1613, 2004; Jia et al., Diabetologia 50:286-292, 2007; Furukawa et al., J Clin Endocrinol Metab 93:310-314, 2008).

Tag SNP Selection

Using the HapMap Phase II for Han Chinese from Beijing (CHB)(www.hapmap.org), all SNPs with minor allele frequency (MAF)≥0.05 in 6 candidate genes with ~2 kb flanking regions were extracted for tagSNP selection under the pair-wise tagging mode with r2≥0.8 by Haploview v 4.ORC2 (Barrett et al., Bioinformatics 21:263-265, 2005). Together with previous SNPs associated with T2D and/or related traits (rs4646953 of IDE, rs2808661 and rs6689429 of APCS), 89 SNPs were genotyped in the first stage and those with nominally-significant SNPs for T2D were validated in the stage-2 study.

Genotyping

All stage 1 SNPs were genotyped using the matrix-assisted laser desorption ionization-time of flight (MALDI-TOF) MassARRAY System (Sequenom, San Diego, Calif.). Only SNPs passing the quality control (QC) criteria [call rates≥0.8, MAF≥0.05, a concordance rate>99% and exhibited no departure from Hardy-Weinberg equilibrium in control subjects (P>0.001)] were included for analysis. The stage-2 genotyping was performed using either Sequenom's MassARRAY System (Sequenom, San Diego, Calif.) or the MGB TaqMan Assay (Applied Biosystems, USA) at each site.

Clinical Assessment and Metabolic Profiling

The clinical assessments have been previously described (Yang et al., Diabetes Care 30:65-70, 2007; Ng et al., Diabetes 53:1609-1613, 2004; Li et al., Diabetes Metab Res Rev 22:46-52, 2006). All patients attending the CUHK-PWH-DMEC underwent a structured assessment based on the European Diabcare protocol (Piwernetz et al., Diabet Med 10:371-377, 1993). Control subjects underwent full physical examination with documentation of blood pressure and anthropometric measurements including body mass index (BMI) after an overnight fast. Fasting blood samples were collected for genetic analysis and biochemical measurements including fasting PG and insulin. A subset of control subjects underwent a 75-gram oral glucose tolerance test (OGTT) and blood samples were collected at multiple time-points for glucose and insulin measurements. In the FBAT analysis, amongst non-diabetic first degree relatives, a random subcohort of 85 subjects had measurement of fasting plasma IAPP determined in the laboratory of Professor Garth J S Cooper by radioimmunoassay methods (Bai et al., Biochem J 343 Pt 1:53-61, 1999).

Calculation

The area under the curve (AUC) of PG and insulin during OGTT was calculated by the trapezoid rule. The insulin resistance (HOMA-IR) was calculated by the equation of [fasting insulin (mU/1)×fasting PG (mmol/l)÷22.5] while beta-cell function was estimated by two algorithms: 1) HOMA-β=[fasting insulin (mU/l)×20÷(fasting PG (mmol/l)−3.5)] and 2) beta-cell function($\times 10^{-6}$)=[insulin $AUC_{30min}$ (min·pmol/l)÷glucose $AUC30_{min}$ (min mmol/l)] (Stumvoll et al., Diabetes Care 23:295-301, 2000).

Functional Studies of rs1583645 in CPE Gene

Bioinformatics Analyses

Cross-species alignment of rs1583645 and its flanking sequence (NCBI Build-36.1 CHR4:166517861-166517941) was visualized using the University of California, Santa Cruz (UCSC) genome browser (http://genome.cse.ucsc.edu/cgi-bin/hgGateway). Additionally, possible regulatory functions of this CPE polymorphism were examined according to the annotations for gene regulation including CpG islands, chromatin structure and ENCODE histone modification tracked on the UCSC genome browser.

Transcription Factor Binding Site (TFBS) Prediction

To predict TFBSs of the rs1583645 region, the MATCH™ program (Kel et al., Nucleic Acids Res 31:3576-3579, 2003) was used interlinked with the TRANSFAC® Release 7.0 database (Wingender et al., Nucleic Acids Res 24:238-241, 1996) under a cut-off score of 0.8 for matrix and core similarities. The prediction was then verified by the web-based rVISTA 2.0 tools (http://rvista.dcode.org/) analyzed for TFBSs under the same threshold for matrix score.

Transient Transfection Studies

Briefly, two clones were generated with identical sequences except [A/G] variants at rs1583645 into pGL4.23 luciferase vectors with the minimal promoter (Promega) by PCR cloning and QuickChange Site-Directed Mutagenesis Kit (Stratagene, La Jolla, Calif., USA) using following primers: forward: 5'-TAAGAGCTC(SacI)CAGACCTGAT-GAATTC-3'(SEQ ID NO:1); reverse: 5'-CTACTCGAG (XhoI)TAGCTGTCTCTTTGAAC-3' (SEQ ID NO:2); M1-5'-CCTATGAAGCCACAAACAAGTAATACAT GTGCCAGTAAAGTTGG-3' (SEQ ID NO:3) and M2-5'-CCAACTTTACTGGCACATGTATTACTTGTTTGT-GGCTTCATAGG-3 (SEQ ID NO:4) (Desired mutation underlined). After confirming clone sequences, these clones were independently transfected with Renilla luciferase vectors [pGL4.73(hRluc/SV40)] into HepG2 and rat INS-1E cells by Lipofectamine™ 2000 (Invitrogen) and detected their luciferase activities in cells with different variants in triplicate in at least 3 independent experiments by Dual-Luciferase Reporter Assay kit (Promega) following the manufacturer's instructions.

Statistical Analysis

All data were expressed as mean±SD or median (interquatile range) as appropriate. Skewed data were transformed using natural logarithm for statistical analysis. Outlier data defined as ≤ or ≥4SD from the mean were excluded. All statistical tests were performed by PLINK (v.0.99 http://pngu.mgh.harvard.edu/~purcell/plink) or SPSS 15.0 for Windows (SPSS Inc., Chicago, Ill., USA) unless specified. The study power in allelic models was estimated using PASS 2008 (NCSS, LLC. Kaysville, Utah). Assuming allelic models, the sample size had over 90% power to detect at least 20% increased risk for T2D for SNPs with MAF of 0.1. The SNPs which passed QC checking were analyzed in each study cohort by $x^2$ test and logistic regression (LR) analysis for the categorical data under genetic models with or without adjustments. To adjust for multiple testings in the stage-1 study, empirical P values were presented by 10,000 permutations under the most significant model amongst genetic models implemented by PLINK. The P or $P_{empirical}$ values ≤0.05 was considered significant (two-tailed) unless specified. Risk association was expressed as odds ratio (OR) with 95% confidence intervals (CI).

The best model was selected based on P values amongst genetic models for the meta-analysis of T2D in the combined cohort. The latter was performed by the fixed effects Cochran-Mantel-Haenszel (CMH) test implemented in PLINK and MedCalc for Windows, version 9.6.0.4 (MedCalc Software, Mariakerke, Belgium) to estimate the combined ORs, 95% CI and significance level, using study population as a strata. Heterogeneity of ORs among study populations was assessed by Cochran's Q statistic which was calculated as the weighted sum of squared differences among individual study effects and the pooled effect across studies. In case of significant heterogeneity (Q statistic P<0.05), the effect size calculated from the random effects model was also reported (DerSimonian and Laird, *Control Clin Trials* 7:177-188, 1986). To test the joint effects of the significant SNPs and assuming additive model, a score of 1 was assigned to each risk allele to generate GRS with a maximum of 4. LR analysis was applied with adjustment for a dummy variable for "Study Population" with coding 1-5 to represent the 5 unrelated case-control cohorts from Hong Kong (stage-1 and 2), Shanghai, Japan, and Korea to examine the risk association of T2D with GRS. Linear regression analysis was also applied under additive models to test the effects of GRS with beta-cell function in the control subjects with or without adjustment as appropriate.

For the familial genetic data, Mendelian errors and potential genotyping errors were checked by PEDCHECK (v.1.1; http://watson.hgen.pitt.edu) and removed accordingly. The FBAT (v.2.0.3; http://www.biostat.harvard.edu/~fbat) was used based on the transmission disequilibrium test (TDT) but generalized to allow analysis in additive model of inheritance using -e option for testing the null hypothesis of "no linkage and no association." The power was estimated by FBAT (Lange et al., *Am J Hum Genet* 71:575-584, 2002) assuming a disease prevalence of 10%, an additive model with allelic OR of 1.2 for SNP with MAF of 0.1. For the dual-luciferase reporter assays, all experiments were performed using a triplicate set-up consisting of 3 independent tests. All results were expressed as mean±SEM and Mann-Whitney U-test was used to compare differences between groups.

Results

Table 1 shows clinical characteristics of the study populations. In the stage-1 study, 459 unrelated Chinese T2D patients and 419 age and sex-matched controls were included. Positive signals were replicated in the stage-2 study including 3,092 Hong Kong Chinese (1,114 cases and 1,978 controls), 3,388 Shanghai Chinese (1,716 cases and 1,672 controls), 1,393 Korean (761 cases and 632 controls) and 1,150 Japanese (568 cases and 582 controls). A family-based cohort of Hong Kong Chinese was included consisting of 472 related subjects in whom PG and insulin were measured at multiple time points during a 75 gram OGTT for analysis of beta-cell function.

Stage-1 Experiment

In the stage-1 study, 89 SNPs were successfully genotyped in 6 genes in 878 unrelated cases and controls. These SNPs captured 79% of all common SNPs (MAF≥0.05) in these target genes. Most of the SNPs meeting the QC criteria except four SNPs [rs2808661 (APCS), rs12306305 and rs1056007 (IAPP), and rs4646953 (IDE)] were included for analysis. Table 4 shows the allelic P and $P_{empirical}$ values for T2D of all SNPs. Six of these SNPs showed nominal associations with 4 SNPs (rs1583645, rs6841638, rs10021007 and rs17046561) in the CPE gene, 1 SNP (rs6583813) in the IDE gene and 1 SNP (rs8117664) in the PCSK2 gene with ORs (95% CI) ranging from 1.24(1.01-1.51) to 1.34(1.02-1.75)($P_{empirical}$=0.013-0.05).

Stage-2 Replication and Meta-Analysis

These 6 SNPs were replicated in 9,023 Asian subjects from Hong Kong, Shanghai, Japan, and Korea, with over 90% power to detect an OR ranging from 1.24 to 1.34 at 5% significant level. In the Shanghai Chinese, rs6583813 was discarded due to unsuccessful panel optimization and replaced by rs2149632 in high linkage disequilibrium (LD) with rs6583813 [$r^2$=0.94; D'=1 using HapMap CHB]. Table 2 summarizes the results in each case-control cohort and meta-analysis in the combined cohort under genetic models for each associated SNP. There were nominal associations of T2D with rs1583645 and rs10021007 of the CPE gene and rs6583813 of the IDE gene in at least one genetic model with some population heterogeneity possibly due to sub-ethnicity and other disease modifiers. For each SNP, the most significant genetic model was selected and the fixed effect model was applied for SNPs which did not show heterogeneity of ORs (Q statistic P>0.05). Otherwise, the random effect model was used. Amongst these 6 SNPs, only rs1583645 and rs17046561 of the CPE gene and rs8117664 of the PCSK2 gene did not show heterogeneity in ORs. Using the combined data in stage-1 and 2 experiments, rs1583645 and rs6583813 of CPE and IDE genes were significantly associated with T2D ($P_{Meta}$=0.001 and 0.045 respectively).

Joint Effects of IDE and CPE Variants

Joint effects of these two SNPs were then tested on T2D risk in the Asian case-control cohort and beta-cell function in a subset of the Hong Kong Chinese control subjects in whom PG and insulin levels were available during 75 gram OGTT. Assuming an additive model, a score of 1 was arbitrarily allocated to each risk variant to generate a genetic risk score (GRS), giving a maximum score of 4. Using LR analysis with adjustment for each of the 5 study populations (code:1-5), GRS was linearly associated with T2D risk (P adjusted<0.001, FIG. 2). Subjects with the highest GRS accounted for 8.2% of the study population and had 45% higher risk for T2D compared to those with the lowest GRS ($P_{adjusted}$=0.02). Control subjects were also categorized by the GRS≤2 and ≥3 with similar numbers in each group for quantitative trait analyses. There was a progressive decline in beta-cell function indexes and AUC of insulin at 30-minute (P=0.03 and 0.05 respectively) with increasing GRS (Table 3).

In FBAT analysis, none of these SNPs was associated with T2D due to limited samples with only 10% power to detect 20% increased risk for MAF of 0.1 under additive models (data not shown). In a subset of these related subjects, 85 non-diabetic subjects had measurement of plasma IAPP levels. In these subjects, GRS was associated with increased plasma IAPP levels and IAPP to insulin molar ratios (P=0.008 and 0.006 respectively) (FIGS. 3A and 3B).

Table 6 shows the risk association of genetic variants of IDE with cancer in patients with family history of diabetes and that of CPE with cardiovascular disease in non-obese subjects. In subjects with positive family history, subjects who had a high GRS of IDE and CPE genetic variants also had increased risk of cancer. FIGS. 6 and 7 show the cumulative incidence of cancer in subgroups of patients with family history of diabetes who were carriers of genetic variants of IDE or CPE.

Functional Analyses

Since rs1583645 in the CPE gene is located close to the promoter region which may regulate gene expression, the function of this SNP was explored using functional and bioinformatics analyses. The flanking regions of CPE rs1583645 showed mild conservation among species with possible sites for islet open chromatin and trimethylation of histone H3 on Lysine 27(H3K27me3) in lymphoblastoid cell line. These findings indicate that genetic variants in this region may regulate basal transcriptional expression of the CPE gene. TFBSs were also predicted for [A/G] polymorphisms of rs1583645 (Table 5) and revealed 11 transcription factors (TFs) which can either bind specifically to one or both of these variants (Oct1, Handl/E47 for A-allele; E47, USF, MyoD, N-Myc, c-Myc/Max, AREB6 for G-allele, S8, CCAAT, NF-Y for both alleles). While functions of some of these TFs were unknown, several of them were implicated in immunity, intermediary metabolism and cell cycle with disease associations including T2D, dyslipidemia and cancer. These results indicate that a single nucleotide substitution in rs1583645 or its closely linked unidentified variants might modify gene expression through chromatin modification and binding to a network of TFs depending on tissue specificity and stimuli for these epigenetic patterns (Relton et al., PLoS Med 7:e1000356, 2010).

The functional activity of rs1583645 of the CPE gene was then examined and PCR fragments of the CPE-A/G variants were amplified which were cloned into pGL4.23 vectors. Direct sequencing was used and its 100% homology with the reference sequence from the gene bank (Accession number: GL000046.1) was confirmed. The effect of rs1583645[A/G] polymorphism on the transcriptional activity of the CPE gene was tested using dual-luciferase reporter assays transiently transfected in HepG2 and rat INS-1E cell lines. In both cell lines transfected with the constructs carrying the G-risk allele of rs1583645, the basal luciferase activity was 50-66.7% higher than those transfected with A-allele of rs1583645 (P<0.001 and P=0.005 respectively, Mann-Whitney U-test) suggesting a regulatory role of this polymorphism.

Discussion

In this multi-stage experiment, tagSNP approach and genetic statistics, bioinformatics and functional analyses were used to examine independent and joint effects of components of the IAPP pathway on risk of T2D and beta-cell function. In the meta-analysis, the risk association of 2 SNPs in CPE and IDE genes with T2D, increased IAPP and reduced beta-cell function was confirmed. These findings were corroborated by bioinformatics and functional analyses indicating this region might harbor regulatory components for gene expression through chromatin modification and binding with TFs.

In this study, the newly released data from the HapMap Project were used to select tagSNPs which captured over 90% of common SNPs with MAF>5% for each of these 6 candidate genes. The combined case-control cohort consisting of 9,901 subjects had over 90% power to detect at least 20% increased risk for T2D for SNPs with MAF of 10%. In the stage-1 study, 6 SNPs in CPE, IDE and PCSK2 genes were selected which showed nominal significance for replication. Although these SNPs exhibited some heterogeneity in their effect sizes among Asian cohorts, possibly due to minor differences in gene architecture and other confounders such as lifestyle, cultural and environmental factors (He et al., PLoS One 4:e4684, 2009), the meta-analysis revealed consistent associations of T2D with rs1583645 and rs6583813 in CPE and IDE genes respectively. Importantly, subjects with risk variants, which accounted for 8.2% of the study population, had 45% increased risk of T2D and reduced beta-cell function in control subjects. The increased plasma IAPP levels in non-diabetic subjects with multiple risk variants are in keeping with results of functional and bioinformatics analyses. Given differential tissue expression, experimental studies will be needed to demonstrate whether these risk variants will cause increased synthesis of IAPP and beta-cell toxicity, especially in the presence of stressors for overproduction (e.g., insulin resistance, obesity) and/or reduced clearance. Since rs6583813 is away from the promoter region of the IDE gene, its function was only inferred using bioinformatics analysis.

Functional Analysis

CPE is widely expressed in tissues including brain and pancreas and responsible for cleaving dibasic amino acid residues during processing of various proproteins including pro-IAPP. Impaired CPE activity by the R283W mutation and palmitate treatment causes accumulation of prohormones exerting ER stress and beta-cell apoptosis (Chen et al., Hum Mutat 18:120-131, 2001; Jeffrey et al., Proc Natl Acad Sci USA 105:8452-8457, 2008). In experimental studies, deletion of upstream region of the CPE gene resulted in reduced transcriptional activity in different cell lines (Jung et al., Mol Endocrinol 6:2027-2037, 1992). In pituitary GH3 cells transfected with a furin-cleavable human proinsulin cDNA, over expressing CPE was associated with increased insulin synthesis but variable basal insulin secretion due to differential expression of the membrane form of CPE (Polastri et al., Cell Transplant 11:803-811, 2002). Taken together, genetic variants in the promoter region of the CPE gene may result in dysregulated CPE activity and beta-cell dysfunction.

Compared to other cis-regulatory elements, rs1583645 is relatively far from the transcription start site (TSS) suggesting a possible distal effect on gene regulation. Since the promoter region of the CPE gene is reasonably conserved, it is plausible that the risk association of T2D with rs1583645 might be mediated through an altered transcriptional activity of the CPE gene. Other studies demonstrated modest effects of the distal region from the TSS site of CPE gene on the transcription activity although the expression was tissue dependent (Jung et al., 1992, supra). In both HepG2 and rat INS-1E cell lines, compared to the empty pGL4.23 vector, both constructs showed reduced transcriptional activity with differential effects between the risk (G-allele) and non-risk (A-allele) variants, the latter being more suppressed than the former. As known, insulin and IAPP secretion is tightly regulated with a fixed ratio. Reduced CPE activity can lead to low insulin response with either accumulation of pro-IAPP or increased IAPP secondary to beta-cell stress. Alternatively, high CPE activity can increase IAPP levels with beta-cell toxicity due to excessive oligomerization especially with reduced clearance. Without measuring the CPE activity, final effects of these functional SNPs remain uncertain. Suffice to say, these findings of differential effects of these variants and their correlations with IAPP:insulin sub-phenotype in control subjects support their functional relevance.

Bioinformatics Analysis

On bioinformatics analysis, the moderate conservation was confirmed in the flanking region of rs1583645 of the CPE gene among species. Chromatin and histone modifications play important role in regulating the structure and function of pancreatic islet cells (Bhandare et al., *Genome Res* 20:428-433, 2010; Gaulton et al., *Nat Genet* 42:255-259, 2010; Stitzel et al., *Cell Metab* 12:443-455, 2010). The CPE gene is one of reported genes with known function in islet cells and contained in islet-selective open chromatin (Gaulton et al., 2010, supra) which encompasses various gene regulatory elements. The latter recruit TFs to form a DNA loop that brings it into indirect interaction with promoter to regulate gene expression despite its upstream location from TSS (Noonan and McCallion, *Annu Rev Genomics Hum Genet* 11:1-23, 2010). To this end, 11 TFs were predicted to bind either specifically to [A/G] variants or both. While these predictions need experimental confirmation, two of these TFs are located within the chromosome 1q region which is the most replicable loci for T2D in multiple populations (Prokopenko et al., *Diabetes* 58:1704-1709, 2009). Genetic variants of these genes, the upstream stimulating factor (USF) which binds the G-allele of the CPE gene and the octamer binding factor 1 (Oct1 also known as POU2F1) which binds to the A-allele of the CPE gene and known to interact with histone proteins altering chromatin organization and inflammatory responses (Kim et al., *Mol Cell Biol* 16:4366-4377, 1996), were associated with T2D in our Chinese populations (Ng et al., *Diabet Med* 27:1443-1449, 2010).

Several researchers have reported risk associations of T2D with genetic variants of the IDE gene (Kwak et al., *Diabetes Res Clin Pract* 79:284-290, 2008; Rudovich et al., *J Mol Med,* 87:1145-115; 2009). In this study, the inventors included these SNPs (rs4646953, rs4646958 and rs1887922) in addition to tagSNPs (rs4304670 for rs4646957; rs6583813 for rs2149632) for genotyping in the stage-1 experiment. Only rs6583813 was selected for replication and excluded other SNPs due to failed QC (rs4646953) or non-significance, the latter possibly confounded by insufficient sample size. Apart from increased risk for T2D, there were joint effects of CPE and IDE genes on reduced beta-cell function in non-diabetic subjects. One recent European study has revealed association of reduced insulin secretion with rs2149632 which was in high LD with rs6583813 (Kwak et al., 2008, supra; Rudovich et al., 2009, supra).

In a collaborative study with deCODE which examined risk variants for multiple diseases in Icelanders using GWAS, the risk association of T2D with three SNPs (rs1111875, rs5015480 and rs7923837) in the HHEX-IDE LD was replicated (Ng et al., *Diabetes* 57:2226-2233, 2008). Most of the SNPs were discovered near the HHEX gene, upstream of the IDE gene. In the present analysis, the rs6583813 was located near the 3' end of the IDE gene with low or moderate LD with the above 3 SNPs discovered in the GWAS ($r^2$=0.67, 0.36 and 0.29 respectively in Hong Kong Chinese). Although the HHEX gene was the favored gene in this block, a recent report on the joint effects of TCF7L2, HHEX and IDE SNPs on risk of T2D supports the importance of all these genes (Nordman et al., *Exp Clin Endocrinol Diabetes* 117:186-190, 2009). In a new study which examined the epigenome of human pancreatic islets, rs6583813 lies within a putative regulatory element (NCBI Build36.1 CHR10:94199479-94203011) which is a possible site for epigenetic regulation (Stitzel et al., 2010, supra).

Joint Effects of Genetic variants of IDE and CPE

Pancreatic amyloidosis is a hallmark in T2D (Hoppener et al., 2000, supra). In Asian populations, the genetic variant, S20G mutation is associated with increased risk of T2D (Lee et al., *J Endocrinol* 54:541-6; 2001) and the mutant peptide has increased amyloidogenic properties (Sakagashira et al., *Am J Pathol* 157:2101-2109, 2000). Recent studies have shown that IAPP aggregated to form oligomers to cause beta-cell toxicity without fibril formation (Zhao et al., *Transl Res* 153:24-32, 2009).

Due to inadequate samples and young age of the family-based cohort, none of the SNPs of IDE or CPE genes showed risk association of T2D. However, in this family-based cohort, non-diabetic subjects with high GRS had increased IAPP levels and high IAPP:INS ratio. Together with results from the functional study, the overall evidence supports the hypothesis that abnormal processing of IAPP might impair beta-cell function especially with reduced clearance. To this light, high IAPP levels, either de-novo or compensatory, can induce ER stress and trigger apoptotic signaling pathways with increased expressions of C/EBP homologous proteins (CHOP) and caspase-3 (Zhao et al., 2009, supra; Huang et al., *Diabetes* 56:2016-2027, 2007; Gu et al., *Life Sci* 87:724-32, 2011). Other mechanisms for IAPP-induced beta-cell toxicity include mitochondrial dysfunction, oxidative stress and activation of JNK/p38 mitogen-activated protein kinase pathways (Li et al., *Int J Biochem Cell Biol* 43:525-341, 2011; Li et al., *Int J Biochem Cell Biol,* 41:1526-35; 2009).

Although functional significance of rs6583813 of the IDE gene were not demonstrated, both insulin and IAPP share similar transcriptional regulators and enzymatic pathways for maturation and degradation (German et al., *Mol Cell Biol* 12:1777-1788, 1992; Kurochkin, *Trends Biochem Sci* 26:421-425, 2001; Steiner et al., *Diabetes Obes Metab* 11 Suppl 4:189-196, 2009). Generally, IAPP and insulin levels are kept at a steady proportion to form an IAPP-insulin complex in secretory granules with a constant ratio although these peptides exhibit different kinetics and responses to stimuli or conditions. In experimental studies, exposure to fatty acids induced overexpression of IAPP levels leading to impaired insulin secretion (Hoppener et al., 2000, supra; Qi et al., *Am J Physiol Endocrinol Metab,* 298:E99-E107, 2010). Thus, genetic or acquired factors which perturb activities of these processing and degrading enzymes can theoretically alter the IAPP:insulin ratio to increase risk of IAPP oligomerization, fibril formation, beta-cell dysfunction and T2D (Jaikaran et al., *Biochem J* 377:709-716, 2004).

Limitations

This study has over 90% power to detect at least 20% increased risk for SNPs with MAP>0.05 in the entire cohort. However, in the stage-1 experiment involving 459 young patients with familial T2D and 419 controls, the exclusion of some SNPs with low MAF or effect size might introduce type 2 error. Analysis of these SNPs in larger samples will be useful to study their associations with risk of T2D. Despite differential effects of variants in CPE rs1583645 on basal transcriptional activity, influences due to adjacent variants via LD structures with stronger causal relationships cannot be excluded.

CONCLUSION

In this multi-stage experiment, the understanding of IAPP metabolism was combined with genetic analysis in multiple cohorts to demonstrate genotype-phenotype correlations relevant to T2D and beta-cell function. Using a hypothesis defined a priori, the risk association of T2D with SNPs in CPE and IDE genes was confirmed. In high risk non-diabetic subjects with affected family members, these risk variants were associated with reduced beta-cell function but increased IAPP levels and IAPP:insulin ratio. Simultaneously, bioinformatics analysis indicated these SNPs are located within regulatory sites for chromatin modification and DNA-protein binding. Although the effect size of these SNPs averaged 15-20%, their population frequency ranged from 5% to 50%. In this context, as high as 50% of population attributable risks for common complex diseases such as T2D can be explained by 20 or fewer susceptibility genes with an effect size of 10-20% (Yang et al., *Int J Epidemiol* 34:1129-1137, 2005). Taken together, these findings support an important role of IAPP metabolism in T2D and that using tagSNPs of candidate genes within a metabolic pathway may predict high risk subjects for prevention of T2D.

All patents, patent applications, and other publications, including GenBank Accession Numbers, cited in this application are incorporated by reference in the entirety for all purposes.

TABLE 1

Clinical characteristics of the case-control cohorts from Hong Kong, Shanghai, Taiwan and Japan in the 2-stage genetic association study.

| | Stage-1 Hong Kong Chinese | | Stage-2 Hong Kong Chinese | | | |
|---|---|---|---|---|---|---|
| | Adult controls | T2D | Adolescents | Adult controls | T2D | Family subjects |
| N | 419 | 459 | 984 | 994 | 1114 | 472 |
| Sex(% of male) | 40 | 38 | 47 | 51 | 42 | 39 |
| Age (years) | 41 ± 10 | 39 ± 8 | 15 ± 2 | 72 ± 5 | 53 ± 14 | 47 ± 15 |
| Duration of diabetes (years) | — | 8 ± 8 | — | — | 5 ± 6 | — |
| Body mass index (kg/m$^2$) | 22.5 ± 3.2 | 25.8 ± 4.7 | 19.9 ± 3.6 | 23.2 ± 3.2 | 25.0 ± 4.1 | 26.5 ± 4.6 |
| Fasting plasma glucose (mmol/l)$^a$ | 4.8 (4.5; 5.1) | 7.9 (6.6; 10.7) | 4.7 (4.5; 5) | — | 8.1 (6.6; 10.5) | — |
| Fasting plasma insulin (pmol/l)$^a$ | 40 (26; 57) | — | 49 (36; 68) | — | — | — |

| | Stage-2 | | | | | |
|---|---|---|---|---|---|---|
| | Shanghai Chinese | | Korean | | Japanese | |
| | Adult controls | T2D | Adult controls | T2D | Adult controls | T2D |
| N | 1672 | 1716 | 632 | 761 | 582 | 568 |
| Sex(% of male) | 41 | 53 | 45 | 47 | 35 | 55 |
| Age (years) | 58 ± 12 | 61 ± 13 | 65 ± 4 | 59 ± 10 | 68 ± 9 | 62 ± 10 |
| Duration of diabetes (years) | — | 7 ± 7 | — | 9 ± 8 | — | 16 ± 10 |
| Body mass index (kg/m$^2$) | 23.6 ± 3.3 | 24.0 ± 3.5 | 23.5 ± 3.1 | 24.5 ± 2.9 | 22.4 ± 3.2 | 24.1 ± 3.7 |
| Fasting plasma glucose (mmol/l)$^a$ | 5.0 (4.6; 5.4) | — | 5.0 (4.5; 5.3) | 8.0 (6.7; 9.9) | — | — |
| Fasting plasma insulin (pmol/l)$^a$ | 37 (23; 57) | — | 43 (32; 58) | — | — | — |

T2D = type 2 diabetes
All continuous values were shown as mean ± SD or
$^a$median(interquartile range).

TABLE 2

Risk alleles of associated SNPs in the meta-analysis of combined stages for type 2 diabetes (T2D).

| | Risk Allele | N T2D | Con-trols | Genotypes T2D | Genotypes Controls | Allelic P values | Allelic Odds ratios | Recessive P values | Recessive Odds ratios | Dominant P values | Dominant Odds ratios | [c]Stage-1 and 2 combined $P_{Meta}$ values | [c]Stage-1 and 2 combined Odds ratios$_{Meta}$ | Cochran's Q statistic |
|---|---|---|---|---|---|---|---|---|---|---|---|---|---|---|
| CPE | | | | | | | | | | | | | | |
| rs1583645 Stage-1 | G | | | AA/GA/GG | AA/GA/GG | | | | | | | | | |
| Hong Kong Chinese | | 410 | 386 | 18/153/239 | 30/151/205 | [a]0.05 | 1.26(1.0-1.57) | 0.141 | 1.23(0.93-1.63) | 0.045 | 1.84(1.01-3.32) | 0.001 | 1.16(1.06-1.26) | 0.067 |
| Stage 2 | | | | | | | | | | | | | | | |
| Hong Kong Chinese | | 1079 | 1969 | 45/368/666 | 110/740/1119 | 0.005 | 1.2(1.05-1.36) | 0.009 | 1.22(1.05-1.43) | 0.089 | 1.36(0.95-1.94) | | | |
| Shanghai Chinese | | 1618 | 1634 | 44/361/1213 | 37/446/1151 | 0.021 | 1.17(1.02-1.35) | 0.004 | 1.26(1.08-1.47) | 0.405 | 0.83(0.53-1.29) | | | |
| Japanese | | 568 | 582 | 15/126/427 | 11/138/433 | 0.993 | 1(0.79-1.27) | 0.762 | 1.04(0.8-1.36) | 0.392 | 0.71(0.32-1.55) | | | |
| Korean | | 754 | 629 | 20/191/543 | 13/143/473 | 0.161 | 0.86(0.69-1.06) | 0.182 | 0.85(0.67-1.08) | 0.477 | 0.77(0.38-1.57) | | | |
| rs6841638 Stage-1 | G | | | TT/GT/GG | TT/GT/GG | | | | | | | | | |
| Hong Kong Chinese | | 428 | 416 | 31/125/272 | 27/166/223 | [a]0.036 | 1.3(1.04-1.62) | 0.003 | 1.51(1.15-1.99) | 0.666 | 0.89(0.52-1.52) | 0.51 | 1.06(0.9-1.24) | 0.014 |
| Stage-2 | | | | | | | | | | | | | | | |
| Hong Kong Chinese | | 1081 | 1968 | 47/372/662 | 100/648/1220 | 0.993 | 1(0.88-1.14) | 0.683 | 0.97(0.83-1.13) | 0.366 | 1.18(0.83-1.68) | | | |
| Shanghai Chinese | | 1688 | 1664 | 56/551/1081 | 58/493/1113 | 0.162 | 0.92(0.81-1.04) | 0.083 | 0.88(0.76-1.02) | 0.788 | 1.05(0.72-1.53) | | | |
| Japanese | | 568 | 582 | 15/142/411 | 17/150/415 | 0.659 | 1.05(0.84-1.32) | 0.691 | 1.05(0.81-1.36) | 0.773 | 1.11(0.55-2.24) | | | |
| Korean | | 757 | 632 | 20/181/556 | 15/165/452 | 0.542 | 1.07(0.87-1.32) | 0.422 | 1.1(0.87-1.4) | 0.750 | 0.9(0.45-1.76) | | | |
| rs10021007 Stage-1 | C | | | AA/CA/CC | AA/CA/CC | | | | | | | | | |
| Hong Kong Chinese | | 429 | 415 | 48/185/196 | 62/197/156 | [a]0.01 | 1.30(1.06-1.58) | 0.017 | 1.4(1.06-1.84) | 0.106 | 1.39(0.93-2.08) | [e]0.61 | [e]1.07(0.83-1.34) | [e]0.03 |

TABLE 2-continued

Risk alleles of associated SNPs in the meta-analysis of combined stages for type 2 diabetes (T2D).

| | Risk Allele | N T2D | N Con-trols | Genotypes T2D | Genotypes Controls | Allelic P values | Allelic Odds ratios | Recessive P values | Recessive Odds ratios | Dominant P values | Dominant Odds ratios | [c]Stage-1 and 2 combined P[Meta] values | Odds ratios[Meta] | Cochran's Q statistic |
|---|---|---|---|---|---|---|---|---|---|---|---|---|---|---|
| Stage-2 | | | | | | | | | | | | | | |
| Hong Kong Chinese | | 1069 | 1978 | 114/489/466 | 247/908/823 | 0.136 | 1.09(0.97-1.22) | 0.290 | 1.08(0.93-1.26) | 0.137 | 1.2(0.94-1.51) | | | |
| Shanghai Chinese | | 1216 | 1577 | 103/468/645 | 147/655/775 | 0.053 | 1.12(1-1.26) | 0.041 | 1.17(1.01-1.36) | 0.435 | 1.11(0.85-1.45) | | | |
| Japanese | | 568 | 582 | 41/193/334 | 21/199/362 | 0.044 | 0.82(0.67-0.99) | 0.239 | 0.87(0.68-1.1) | 0.007 | 0.48(0.28-0.82) | | | |
| Korean | | 754 | 629 | 46/288/420 | 46/257/326 | 0.131 | 1.14(0.96-1.35) | 0.150 | 1.17(0.95-1.45) | 0.368 | 1.21(0.8-1.85) | | | |
| rs17046561 Stage-1 | G | | | AA/GA/GG | AA/GA/GG | | | | | | | | | |
| Hong Kong Chinese | | 423 | 412 | 6/100/317 | 10/119/283 | [a]0.03 | 1.34(1.02-1.75) | 0.045 | 1.36(1.01-1.84) | 0.288 | 1.73(0.63-4.74) | [d]0.25 | [d]1.05(0.96-1.15) | [d]0.16 |
| Stage-2 | | | | | | | | | | | | | | |
| Hong Kong Chinese | | 1080 | 1978 | 23/278/779 | 62/512/1404 | 0.269 | 1.09(0.94-1.26) | 0.502 | 1.06(0.9-1.25) | 0.106 | 1.49(0.92-2.41) | | | |
| Shanghai Chinese | | 1618 | 1649 | 17/294/1307 | 20/278/1351 | 0.504 | 0.95(0.8-1.11) | 0.399 | 0.93(0.78-1.11) | 0.661 | 1.16(0.6-2.21) | | | |
| Japanese | | 568 | 582 | 2/98/468 | 3/116/463 | 0.224 | 1.19(0.9-1.56) | 0.220 | 1.2(0.9-1.62) | 0.674 | 1.47(0.25-8.71) | | | |
| Korean | | 752 | 630 | 3/125/624 | 4/92/534 | 0.464 | 0.9(0.69-1.19) | 0.370 | 0.88(0.66-1.17) | 0.538 | 1.6(0.36-7.06) | | | |
| IDE [b]rs6583813 Stage-1 | C | | | CC/CT/TT | CC/CT/TT | | | | | | | | | |
| Hong Kong Chinese | | 429 | 414 | 62/188/179 | 47/167/200 | [a]0.04 | 1.24(1.01-1.51) | 0.18 | 1.32(0.88-1.98) | 0.055 | 1.31(0.99-1.71) | 0.045 | 1.35(1.01-1.81) | 0.001 |
| Stage-2 | | | | | | | | | | | | | | |
| Hong Kong Chinese | | 1076 | 1952 | 128/480/468 | 252/847/853 | 0.751 | 0.98(0.88-1.1) | 0.420 | 0.91(0.73-1.14) | 0.914 | 1.01(0.87-1.17) | | | |
| Shanghai Chinese | | 1292 | 1576 | 153/449/690 | 164/608/804 | 0.693 | 0.98(0.87-1.1) | 0.222 | 1.16(0.92-1.46) | 0.202 | 1.1(0.95-1.28) | | | |
| Japanese | | 568 | 582 | 93/267/208 | 48/249/285 | <0.001 | 1.57(1.33-1.87) | <0.001 | 2.18(1.51-3.13) | <0.001 | 1.66(1.31-2.1) | | | |
| Korean | | 756 | 630 | 128/349/279 | 70/294/266 | 0.003 | 1.27(1.09-1.48) | 0.002 | 1.63(1.2-2.22) | 0.044 | 1.25(1.01-1.55) | | | |

TABLE 2-continued

Risk alleles of associated SNPs in the meta-analysis of combined stages for type 2 diabetes (T2D).

| | | N | | Genotypes | | Allelic | | Recessive | | Dominant | | [c]Stage-1 and 2 combined | | Cochran's Q statistic |
|---|---|---|---|---|---|---|---|---|---|---|---|---|---|---|
| | Risk Allele | Con- T2D trols | | T2D | Controls | p values | Odds ratios | p values | Odds ratios | p values | Odds ratios | $P_{Meta}$ values | Odds ratios$_{Meta}$ | |

PCSK2 rs8117664
stage-1

| | | | | GG/GT/TT | GG/GT/TT | | | | | | | | | |
|---|---|---|---|---|---|---|---|---|---|---|---|---|---|---|
| Hong Kong Chinese | G | 424 | 416 | 16/119/289 | 7/102/307 | [a]0.03 | 1.32(1.02-1.72) | 0.063 | 2.29(0.96-5.5) | 0.072 | 1.32(0.98-1.77) | [d]0.35 | [d]0.96(0.89-1.04) | [d]0.108 |

Stage-2

| Hong Kong Chinese | 1075 | 1978 | 28/272/775 | 74/524/1380 | 0.081 | 0.88(0.76-1.02) | 0.095 | 0.69(0.44-1.07) | 0.178 | 0.89(0.76-1.05) | | | |
|---|---|---|---|---|---|---|---|---|---|---|---|---|---|
| Shanghai Chinese | 1161 | 1542 | 56/339/766 | 65/485/992 | 0.635 | 0.97(0.85-1.11) | 0.449 | 1.15(0.8-1.66) | 0.375 | 0.93(0.79-1.09) | | | |
| Japanese | 568 | 582 | 21/174/373 | 16/202/364 | 0.510 | 0.93(0.76-1.15) | 0.362 | 1.36(0.7-2.62) | 0.269 | 0.87(0.69-1.11) | | | |
| Korean | 749 | 627 | 26/262/461 | 24/221/382 | 0.754 | 0.97(0.81-1.17) | 0.725 | 0.9(0.51-1.59) | 0.813 | 0.97(0.78-1.21) | | | |

P or [a]P$_{empirical}$ values and ORs with nominal significance for T2D risk (P ≤ 0.05) were shown in bold.
[b]rs2149632 in high LD with rs6583818 (r$^2$ = 0.94; D' = 1) was genotyped in Shanghai Chinese.
[c]The meta-analysis among five unrelated case-control cohorts (Stage-1 study: Hong Kong Chinese; Stage-2 study: Additional Hong Kong Chinese, shanghai Chinese, Japanese and Korean) was performed in the best genetic model by the fixed effects of Cochran-Mantel-Haenszel (CMH) test. Heterogeneity of ORs among studies was assessed by Cochran's Q statistics. The effect size calculated from the random effects model if Q's statistic P was smaller than 0.05.
[d]indicated the meta-analysis conducted using allelic and dominant models respectively otherwise was recessive model.

TABLE 3

Associations of genetic risk score (GRS) with beta-cell function in Hong Kong Chinese unrelated controls (N = 419) with 1 risk allele of rs1583645 of the CPE gene and rs6583813 of the IDE gene each given 1 point.

| Genetic risk score (GRS) | 0-1 | 2 | 3-4 | P value |
|---|---|---|---|---|
| Subjects (%) | 30 | 41 | 29 | |
| Sex (% of male) | 42 | 38 | 36 | |
| Age (years) | 41 ± 10 | 40 ± 11 | 40 ± 10 | |
| Body mass index (kg/m$^2$) | 22.5 ± 3.2 | 22.6 ± 3.3 | 22.5 ± 3.1 | |
| Results of 75 g oral glucose tolerance test | | | | |
| Fasting plasma glucose (mmol/l)$^a$ | 4.8 (4.6, 5) | 4.72 (4.45, 5.1) | 4.8 (4.6, 5.1) | 0.88 |
| Fasting plasma insulin (pmol/l)$^a$ | 41.4 (26, 60.7) | 41.5 (25.2, 54.1) | 37.3 (24.1, 56.7) | 0.22 |
| Plasma glucose at 30-minute (mmol/L)$^a$ | 7.67 (6.68, 8.75) | 7.78 (6.85, 8.87) | 7.86 (6.89, 8.61) | 0.31 |
| Plasma insulin at 30-minute (pmol/L)$^a$ | 286 (180, 449) | 292 (182, 427) | 288 (196, 407) | 0.24 |
| Glucose AUC at 30-minute (min · mmol/l)$^a$ | 195 (179, 205) | 190 (175, 207) | 191 (177, 210) | 0.73 |
| Insulin AUC at 30-minute (min · pmol/l)$^a$ | 5817 (3583, 7811) | 5670 (3555, 8432) | 4856 (3574, 6922) | 0.05 |
| Beta-cell function (×10$^{-6}$)$^a$ | 29.7 (21.7, 40.7) | 30.8 (19.8, 42.8) | 27.1 (18.4, 36.1) | 0.03 |

Data were shown as mean ± SD or
$^a$ median(interquatile range) and analyzed by the linear regression with adjustment of age, sex and BMI under additive models after log-transformation.
P values in bold indicated significance for the phenotypes.
AUC: area under the curve.

TABLE 4

SNP list for data analyses in the stage 1 study.

| No | SNP | CHR: bp in NCBI Build 36.1 | Gene | Allele 1/2 | Allele 1 frequency (non-DM controls) | Call rate | HWE P-value (non-DM controls) | Allelic ORs (95% CI) for type2 DM | P value | P$_{empirical}$ value | Power$_{allelic}$ (α = 0.05, one-sided) |
|---|---|---|---|---|---|---|---|---|---|---|---|
| 1 | rs17046561 | CHR4: 166639887 | CPE | G/A | 0.83 | 0.96 | 0.53 | 1.34(1.02-1.75) | 0.034 | 0.033 | 0.705 |
| 2 | rs7729742 | CHR5: 95799761 | PCSK1 | T/A | 0.87 | 0.98 | 0.72 | 1.33(0.99-1.79) | 0.061 | 0.058 | 0.604 |
| 3 | rs817664 | CHR20: 17200516 | PCSK2 | G/T | 0.14 | 0.97 | 0.64 | 1.32(1.02-1.72) | 0.037 | 0.033 | 0.678 |
| 4 | rs10021007 | CHR4: 166590962 | CPE | C/A | 0.61 | 0.97 | 1.00 | 1.30(1.06-1.59) | 0.010 | 0.013 | 0.837 |
| 5 | rs6841638 | CHR4: 166589111 | CPE | G/T | 0.74 | 0.97 | 0.60 | 1.30(1.04-1.62) | 0.022 | 0.036 | 0.758 |
| 6 | rs1583645 | CHR4: 166517901 | CPE | G/A | 0.73 | 0.90 | 0.82 | 1.26(1.00-1.57) | 0.049 | 0.050 | 0.674 |
| 7 | rs11135457 | CHR5: 95758524 | PCSK1 | T/A | 0.12 | 0.97 | 0.88 | 1.26(0.96-1.67) | 0.099 | 0.108 | 0.503 |
| 8 | rs6583813 | CHR10: 94199919 | IDE | C/T | 0.32 | 0.97 | 0.20 | 1.24(1.01-1.51) | 0.039 | 0.042 | 0.686 |
| 9 | rs17687381 | CHR4: 166593331 | CPE | C/A | 0.80 | 0.86 | 0.27 | 1.23(0.95-1.59) | 0.124 | 0.141 | 0.509 |
| 10 | rs4304670 | CHR10: 94321119 | IDE | C/T | 0.23 | 0.95 | 0.09 | 1.22(0.98-1.53) | 0.077 | 0.086 | 0.559 |
| 11 | rs13126038 | CHR4: 166553239 | CPE | G/T | 0.28 | 0.96 | 0.37 | 1.20(0.97-1.48) | 0.090 | 0.056 | 0.540 |
| 12 | rs6850689 | CHR4: 166635903 | CPE | A/G | 0.24 | 0.92 | 0.21 | 1.20(0.96-1.51) | 0.106 | 0.087 | 0.506 |
| 13 | rs6044776 | CHR20: 17315594 | PCSK2 | C/T | 0.18 | 0.98 | 0.49 | 1.20(0.94-1.53) | 0.138 | 0.130 | 0.441 |
| 14 | rs1340937 | CHR20: 17240818 | PCSK2 | G/C | 0.21 | 0.97 | 0.41 | 1.18(0.94-1.48) | 0.159 | 0.159 | 0.420 |
| 15 | rs7091270 | CHR10: 94227405 | IDE | G/T | 0.19 | 0.96 | 0.96 | 1.17(0.92-1.48) | 0.199 | 0.191 | 0.371 |
| 16 | rs6111477 | CHR20: 17200253 | PCSK2 | G/C | 0.50 | 0.97 | 1.00 | 1.15(0.95-1.39) | 0.153 | 0.143 | 0.427 |
| 17 | rs7692951 | CHR4: 166636093 | CPE | A/G | 0.63 | 0.97 | 0.41 | 1.15(0.94-1.40) | 0.176 | 0.183 | 0.404 |
| 18 | rs271942 | CHR5: 95746331 | PCSK1 | C/T | 0.26 | 0.97 | 0.17 | 1.15(0.93-1.43) | 0.194 | 0.197 | 0.365 |
| 19 | rs3781239 | CHR10: 94207777 | IDE | G/C | 0.89 | 0.97 | 0.09 | 1.15(0.84-1.59) | 0.374 | 0.350 | 0.223 |
| 20 | rs6850000 | CHR4: 166523622 | CPE | A/G | 0.71 | 0.86 | 0.80 | 1.14(0.91-1.43) | 0.262 | 0.256 | 0.336 |
| 21 | rs17624488 | CHR4: 166523716 | CPE | T/C | 0.81 | 0.97 | 0.46 | 1.13(0.88-1.44) | 0.351 | 0.344 | 0.252 |
| 22 | rs1992233 | CHR5: 95801861 | PCSK1 | G/T | 0.55 | 0.96 | 0.66 | 1.12(0.92-1.36) | 0.259 | 0.259 | 0.320 |
| 23 | rs2053277 | CHR4: 166546781 | CPE | T/C | 0.11 | 0.94 | 0.59 | 1.11(0.82-1.50) | 0.501 | 0.530 | 0.170 |
| 24 | rs2072960 | CHR20: 17399285 | PCSK2 | A/G | 0.58 | 0.95 | 0.23 | 1.09(0.89-1.32) | 0.412 | 0.405 | 0.225 |
| 25 | rs7441954 | CHR4: 166615409 | CPE | A/T | 0.33 | 0.97 | 0.35 | 1.08(0.88-1.31) | 0.480 | 0.531 | 0.189 |
| 26 | rs1446965 | CHR1: 157829390 | APCS | G/A | 0.45 | 0.97 | 0.95 | 1.06(0.88-1.29) | 0.514 | 0.560 | 0.150 |
| 27 | rs2072959 | CHR20: 17399220 | PCSK2 | G/A | 0.64 | 0.97 | 0.02 | 1.06(0.87-1.29) | 0.577 | 0.588 | 0.145 |
| 28 | rs4933231 | CHR10: 94196162 | IDE | C/T | 0.15 | 0.96 | 0.14 | 1.05(0.80-1.37) | 0.726 | 0.693 | 0.101 |
| 29 | rs6136105 | CHR20: 17399801 | PCSK2 | G/T | 0.13 | 0.95 | 0.54 | 1.05(0.80-1.39) | 0.722 | 0.698 | 0.097 |
| 30 | rs17085908 | CHR5: 95807831 | PCSK1 | C/T | 0.30 | 0.96 | 0.18 | 1.04(0.85-1.28) | 0.696 | 0.690 | 0.102 |
| 31 | rs1446966 | CHR1: 157830107 | APCS | G/A | 0.18 | 1.00 | 0.41 | 1.03(0.80-1.31) | 0.837 | 0.827 | 0.080 |
| 32 | rs6810964 | CHR4: 166542756 | CPE | G/A | 0.46 | 0.97 | 0.46 | 1.03(0.85-1.25) | 0.768 | 0.763 | 0.091 |
| 33 | rs6849361 | CHR4: 166553380 | CPE | T/C | 0.71 | 0.97 | 0.78 | 1.03(0.84-1.27) | 0.769 | 0.819 | 0.086 |
| 34 | rs1010291 | CHR20: 17374687 | PCSK2 | C/T | 0.34 | 0.97 | 0.68 | 1.02(0.84-1.25) | 0.818 | 0.804 | 0.074 |
| 35 | rs3792744 | CHR5: 95768069 | PCSK1 | C/A | 0.84 | 0.97 | 0.65 | 1.02(0.78-1.33) | 0.886 | 0.874 | 0.068 |
| 36 | rs3792747 | CHR5: 95793676 | PCSK1 | T/C | 0.86 | 0.97 | <0.01 | 1.02(0.78-1.34) | 0.891 | 0.914 | 0.067 |
| 37 | rs6136101 | CHR20: 17381800 | PCSK2 | T/A | 0.81 | 0.91 | 0.58 | 1.02(0.80-1.30) | 0.887 | 0.875 | 0.069 |
| 38 | rs9308104 | CHR4: 166529209 | CPE | A/G | 0.56 | 0.91 | 0.01 | 1.02(0.84-1.24) | 0.834 | 0.860 | 0.075 |
| 39 | rs2322291 | CHR4: 166530129 | CPE | A/G | 0.43 | 0.97 | 0.16 | 1.02(0.84-1.23) | 0.853 | 0.862 | 0.075 |
| 40 | rs4690818 | CHR4: 166574572 | CPE | T/C | 0.81 | 0.97 | 0.21 | 1.02(0.80-1.31) | 0.866 | 0.803 | 0.069 |
| 41 | rs2209972 | CHR10: 94169008 | IDE | C/T | 0.23 | 0.95 | 0.89 | 1.01(0.86-1.37) | 0.434 | 0.419 | 0.060 |
| 42 | rs16842306 | CHR1: 157832008 | APCS | T/C | 0.91 | 0.97 | 0.32 | 1.00(0.72-1.39) | 1.000 | 0.965 | 0.050 |

TABLE 4-continued

SNP list for data analyses in the stage 1 study.

| No | SNP | CHR: bp in NCBI Build 36.1 | Gene | Allele 1/2 | Allele 1 frequency (non-DM controls) | Call rate | HWE P-value (non-DM controls) | Allelic ORs (95% CI) for type2 DM | P value | $P_{empirical}$ value | Power$_{allelic}$ ($\alpha$ = 0.05, one-sided) |
|---|---|---|---|---|---|---|---|---|---|---|---|
| 43 | rs9999764 | CHR4: 166521290 | CPE | G/A | 0.65 | 0.84 | 0.07 | 1.00(0.81-1.24) | 0.992 | 0.990 | 0.050 |
| 44 | rs2276931 | CHR4: 166627967 | CPE | C/T | 0.18 | 0.97 | 0.09 | 0.99(0.77-1.27) | 0.950 | 0.934 | 0.059 |
| 45 | rs1887922 | CHR10: 94214145 | IDE | C/T | 0.09 | 0.96 | 0.23 | 0.99(0.70-1.39) | 0.952 | 0.966 | 0.056 |
| 46 | rs1037144 | CHR1: 157834472 | APCS | G/A | 0.85 | 0.96 | 0.28 | 0.99(0.76-1.29) | 0.952 | 0.923 | 0.058 |
| 47 | rs2164864 | CHR4: 166543877 | CPE | C/T | 0.36 | 0.96 | 0.99 | 0.99(0.81-1.21) | 0.915 | 0.930 | 0.061 |
| 48 | rs3762986 | CHR5: 95796618 | PCSK1 | T/C | 0.56 | 0.96 | 0.65 | 0.98(0.81-1.19) | 0.838 | 0.846 | 0.076 |
| 49 | rs155979 | CHR5: 95795654 | PCSK1 | G/C | 0.76 | 0.96 | 0.26 | 0.98(0.78-1.22) | 0.856 | 0.905 | 0.072 |
| 50 | rs6689429 | CHR1: 157824145 | APCS | G/A | 0.81 | 0.97 | 0.08 | 0.98(0.77-1.24) | 0.863 | 0.829 | 0.070 |
| 51 | rs156001 | CHR5: 95810027 | PCSK1 | G/T | 0.53 | 0.96 | 0.38 | 0.97(0.80-1.17) | 0.728 | 0.726 | 0.092 |
| 52 | rs12480205 | CHR20: 17274948 | PCSK2 | A/G | 0.26 | 0.95 | 0.99 | 0.97(0.78-1.21) | 0.789 | 0.756 | 0.086 |
| 53 | rs1446973 | CHR1: 157848561 | APCS | A/G | 0.42 | 0.95 | 0.78 | 0.96(0.79-1.16) | 0.653 | 0.681 | 0.111 |
| 54 | rs17502674 | CHR4: 166602401 | CPE | G/C | 0.77 | 0.90 | 0.61 | 0.96(0.76-1.21) | 0.713 | 0.720 | 0.100 |
| 55 | rs11907226 | CHR20: 17410150 | PCSK2 | C/T | 0.81 | 0.95 | 0.70 | 0.96(0.75-1.22) | 0.728 | 0.693 | 0.095 |
| 56 | rs6080701 | CHR20: 17392862 | PCSK2 | C/T | 0.56 | 0.91 | 0.03 | 0.95(0.78-1.15) | 0.586 | 0.611 | 0.133 |
| 57 | rs3920552 | CHR20: 17287545 | PCSK2 | T/A | 0.59 | 0.88 | 0.17 | 0.95(0.77-1.16) | 0.601 | 0.621 | 0.132 |
| 58 | rs6044730 | CHR20: 17229762 | PCSK2 | G/A | 0.10 | 0.94 | 0.78 | 0.95(0.69-1.31) | 0.754 | 0.715 | 0.094 |
| 59 | rs6080705 | CHR20: 17401598 | PCSK2 | C/A | 0.60 | 0.97 | 0.73 | 0.94(0.77-1.14) | 0.504 | 0.547 | 0.157 |
| 60 | rs6235 | CHR5: 95754654 | PCSK1 | C/G | 0.32 | 0.96 | 0.73 | 0.94(0.77-1.16) | 0.571 | 0.592 | 0.148 |
| 61 | rs156019 | CHR5: 95773119 | PCSK1 | A/T | 0.50 | 0.97 | 0.36 | 0.93(0.77-1.12) | 0.424 | 0.408 | 0.188 |
| 62 | rs1530042 | CHR4: 166609008 | CPE | T/C | 0.21 | 0.93 | 0.81 | 0.93(0.74-1.19) | 0.579 | 0.620 | 0.152 |
| 63 | rs4691198 | CHR4: 166588491 | CPE | C/A | 0.18 | 0.97 | 0.16 | 0.93(0.72-1.20) | 0.572 | 0.557 | 0.142 |
| 64 | rs4690821 | CHR4: 166625034 | CPE | T/C | 0.17 | 0.96 | 0.10 | 0.93(0.72-1.20) | 0.575 | 0.549 | 0.139 |
| 65 | rs1370687 | CHR4: 166609805 | CPE | C/T | 0.19 | 0.97 | 0.89 | 0.92(0.72-1.17) | 0.491 | 0.524 | 0.167 |
| 66 | rs1438119 | CHR4: 166567796 | CPE | C/T | 0.62 | 0.96 | 0.15 | 0.91(0.75-1.11) | 0.375 | 0.370 | 0.247 |
| 67 | rs6136041 | CHR20: 17195207 | PCSK2 | G/A | 0.38 | 0.97 | 0.10 | 0.91(0.74-1.10) | 0.329 | 0.275 | 0.244 |
| 68 | rs3775311 | CHR4: 166606394 | CPE | C/T | 0.95 | 0.86 | 0.05 | 0.91(0.59-1.40) | 0.679 | 0.679 | 0.117 |
| 69 | rs3790336 | CHR20: 17407928 | PCSK2 | A/T | 0.34 | 0.97 | 0.70 | 0.90(0.73-1.10) | 0.312 | 0.308 | 0.270 |
| 70 | rs6044751 | CHR20: 17279333 | PCSK2 | G/A | 0.84 | 0.96 | 0.53 | 0.90(0.70-1.17) | 0.431 | 0.422 | 0.204 |
| 71 | rs13148844 | CHR4: 166522580 | CPE | C/G | 0.64 | 0.95 | 0.42 | 0.89(0.73-1.09) | 0.257 | 0.260 | 0.321 |
| 72 | rs1370682 | CHR4: 166515829 | CPE | G/A | 0.66 | 0.96 | 0.86 | 0.89(0.72-1.08) | 0.236 | 0.236 | 0.315 |
| 73 | rs16998899 | CHR20: 17209305 | PCSK2 | C/A | 0.22 | 0.97 | 0.74 | 0.89(0.71-1.13) | 0.335 | 0.315 | 0.260 |
| 74 | rs2275221 | CHR10: 94286967 | IDE | C/T | 0.94 | 0.97 | 0.78 | 0.88(0.59-1.31) | 0.526 | 0.519 | 0.155 |
| 75 | rs1832197 | CHR10: 94288311 | IDE | G/A | 0.83 | 0.97 | 0.09 | 0.87(0.68-1.11) | 0.262 | 0.251 | 0.301 |
| 76 | rs12624727 | CHR20: 17173515 | PCSK2 | G/A | 0.14 | 0.94 | 0.96 | 0.87(0.66-1.16) | 0.355 | 0.380 | 0.257 |
| 77 | rs6111527 | CHR20: 17316967 | PCSK2 | G/A | 0.30 | 0.97 | 0.68 | 0.86(0.69-1.06) | 0.151 | 0.134 | 0.412 |
| 78 | rs6835167 | CHR4: 166629821 | CPE | C/T | 0.17 | 0.96 | 0.87 | 0.86(0.66-1.11) | 0.247 | 0.261 | 0.317 |
| 79 | rs1446972 | CHR1: 157849970 | APCS | A/G | 0.92 | 0.96 | 0.71 | 0.86(0.61-1.22) | 0.403 | 0.389 | 0.218 |
| 80 | rs4646958 | CHR10: 94204339 | IDE | T/A | 0.90 | 0.96 | 0.77 | 0.84(0.62-1.14) | 0.257 | 0.244 | 0.308 |
| 81 | rs6811043 | CHR4: 166542507 | CPE | A/G | 0.19 | 0.94 | 0.51 | 0.82(0.63-1.05) | 0.119 | 0.122 | 0.469 |
| 82 | rs2269012 | CHR20: 17363959 | PCSK2 | C/T | 0.86 | 0.97 | 0.25 | 0.81(0.62-1.06) | 0.120 | 0.114 | 0.474 |
| 83 | rs6136050 | CHR20: 17210715 | PCSK2 | G/A | 0.91 | 0.96 | 0.31 | 0.77(0.56-1.06) | 0.108 | 0.109 | 0.500 |
| 84 | rs11698919 | CHR20: 17322513 | PCSK2 | G/A | 0.08 | 0.97 | 0.38 | 0.77(0.54-1.12) | 0.172 | 0.223 | 0.412 |
| 85 | rs1015777 | CHR20: 17227771 | PCSK2 | T/A | 0.90 | 0.97 | 0.75 | 0.76(0.56-1.02) | 0.065 | 0.063 | 0.576 |

SNPs were sorted by the effect size for type 2 diabetes (T2D). Significant SNPs for T2D (P ≤ 0.05) under allelic models were shown in bold. Pempirical values were presented by 10,000 permutations under the best model of genetic models implemented in PLINK for multiple test corrections.

TABLE 5

Summary of transcription factor binding sites (TFBSs) predicted in the region of rs1583645 [A/G] with adjacent sequences.

| Polymorphism of rs1583645 | Factor ID | Factor Name | Known functions |
|---|---|---|---|
| A-allele specific | Oct1 | Octamer binding factor 1 | Prostate development, cancer progression and inflammation |
| | Hand1/E47 | Heart and neural crest derivatives expressed 1/E47 | — |
| G-allele specific | E47 | E47 | Regulation of immunoglobulin gene expression |
| | USF | Upstream stimulating factor | Glucose and lipid metabolisms |
| | MyoD | Myoblast determination gene product | Muscle cell development |
| | N-Myc | N-Myc | V-Myc myelocytomatosis viral related oncogene, neuroblastoma derived |
| | c-Myc/Max | MYC associated factor X | Cell proliferation, differentiation and apoptosis |
| | AREB6 | zinc finger E-box binding homeobox 1 | Cancer |
| Both alleles | S8 | S8 | — |
| | CCAAT | Cellular and viral CCAAT box | — |
| | NF-Y | Nuclear factor Y (Y-box binding factor) | — |

TABLE 6

Genetic distribution and association of CPE rs1583645 and/or
IDE rs6583813 in subsets of type 2 diabetic subjects stratified
by the presence of obesity and/or family history.
Type 2 diabetic subjects (N = 5414)

| CPE rs1583645 | | Non-OB (N = 2891) | | | Non-OB & non-CVD (N = 2364) | | | Non-OB & CVD (N = 527) | | | P value; OR(95% CI) | | |
|---|---|---|---|---|---|---|---|---|---|---|---|---|---|
| | Genotypes | AA | AG | GG | AA | AG | GG | AA | AG | GG | Additive | Dominant | Recessive |
| | Frequency | 5.4 | 36.1 | 58.5 | 5.8 | 36.8 | 57.4 | 3.8 | 32.8 | 63.4 | 0.01; 1.26 | 0.07; 1.55 | 0.01; 1.28 |
| | (N) | (156) | (1043) | (1692) | (136) | (870) | (1358) | (20) | (173) | (334) | (1.07-1.49) | (0.96-2.51) | (1.05-1.56) |
| | | OB (N = 2523) | | | OB & non-CVD (N = 2066) | | | OB & CVD N = 457 | | | | | |
| | Genotypes | AA | AG | GG | AA | AG | GG | AA | AG | GG | | | |
| | Frequency | 4.1 | 34.6 | 61.3 | 4.3 | 34.4 | 61.3 | 3.3 | 35.7 | 61.1 | 0.82; 1.02 | 0.32; 1.33 | 0.88; 0.98 |
| | (N) | (103) | (874) | (1546) | (88) | (711) | (1267) | (15) | (163) | (279) | (0.85-1.22) | (0.76-2.33) | (0.8-1.21) |
| IDE rs6583813 | | Non-FH (N = 3166) | | | Non-FH & non-CAN (N = 2875) | | | Non-FH & Can (N = 291) | | | | | |
| | Genotypes | TT | CT | CC | TT | CT | CC | TT | CT | CC | | | |
| | Frequency | 44 | 43.1 | 12.9 | 44 | 43.2 | 12.8 | 44.3 | 41.6 | 14.1 | 0.86; 1.02 | 0.88; 0.98 | 0.56; 1.11 |
| | (N) | (1393) | (1364) | (409) | (1264) | (1243) | (368) | (129) | (121) | (41) | (0.85-1.21) | (0.77-1.25) | (0.78-1.57) |
| | | FH (N = 2221) | | | FH & non-CAN (N = 2083) | | | FH & CAN (N = 138) | | | | | |
| | Genotypes | TT | CT | CC | TT | CT | CC | TT | CT | CC | | | |
| | Frequency | 42.6 | 44.9 | 12.5 | 43.3 | 44.5 | 12.2 | 31.9 | 51.4 | 16.7 | 0.01; 1.41 | 0.01; 1.66 | 0.12; 1.45 |
| | (N) | (946) | (998) | (277) | (902) | (927) | (254) | (44) | (71) | (23) | (1.1-1.8) | (1.15-2.41) | (0.91-2.31) |
| Joint effects | | Non-FH (N = 3165) | | | Non-FH & non-CAN (N = 2874) | | | Non-FH & CAN (N = 291) | | | | | |
| | Groups of risk score[a] | 0-1 | 2 | 3-4 | 0-1 | 2 | 3-4 | 0-1 | 2 | 3-4 | | | |
| | Frequency | 20.5 | 42 | 37.5 | 20.6 | 41.7 | 37.7 | 19.2 | 44.7 | 36.1 | 0.93; 0.99 | 0.56; 0.92 | 0.59; 1.09 |
| | (N) | (649) | (1328) | (1188) | (593) | (1198) | (1083) | (56) | (130) | (105) | (0.84-1.16) | (0.71-1.19) | (0.8-1.47) |
| | | FH (N = 2202) | | | FH & non-CAN (N = 2064) | | | FH & CAN (N = 138) | | | | | |
| | Groups of risk score[a] | 0-1 | 2 | 3-4 | 0-1 | 2 | 3-4 | 0-1 | 2 | 3-4 | | | |
| | Frequency | 18.6 | 41.9 | 39.5 | 18.9 | 42.2 | 38.9 | 14.5 | 36.2 | 49.3 | 0.02; 1.35 | 0.01; 1.56 | 0.15; 1.45 |
| | (N) | (410) | (922) | (870) | (390) | (872) | (802) | (20) | (50) | (68) | (1.06-1.75) | (1.10-2.17) | (0.88-2.38) |

[a]Risk score was estimated and subgrouped by each risk variant of CPE rs1583645 & IDE rs1583813 defined as 1 risk score ranging 0-4 for homozygous non-risk carriers respectively in these SNPs.
OB: Type 2 diabetic subjects with obesity (HMI = 25)
FH: Type 2 diabetic subjects with family history of diabetes.
CAN: Diagnosed with cancer.

TABLE 7

Gene names and sequences which interact to explain large
variance of renal function in type 2 diabetes with renal
function as a major predictor for cardiovascular disease.

| Gene label | Full name of gene | Genomic sequence corresponding to the cDNA sequence plus 2 kb upstream and downstream flanking sequences (GRCh37/hg19) |
|---|---|---|
| LIPC | Hepatic lipase | chr15: 58,724,175-58,861,072 |
| LPL | Lipoprotein lipase | chr8: 19794582-19826769 |
| CETP | Cholesteryl ester transfer protein | chr16: 56,993,835-57,019,756 |
| PPARG | Peroxisome proliferator activated receptor γ | chr3: 12,391,001-12,477,854 |
| GNB3 | G protein β3 subunit | chr12: 6,947,375-6,958,556 |
| NOS3 | Endothelial nitric oxide synthase | chr7: 150,686,144-150,713,686 |
| LTA | Lymphotoxin α | chr6: 31,537,876-31,544,098 |
| AGTR1 | Angiotensin II receptor, type 1 | chr3: 148,413,658-148,462,788 |
| ADRB2 | β2-adrenergic receptor | chr5: 148,204,156-148,210,188 |
| ADRB3 | β3-adrenergic receptor | chr8: 37,818,516-37,826,184 |
| NPPA | Natriuretic peptide precursor A | chr1: 11,903,769-11,909,840 |
| ADD1 | α-adducin | chr4: 2,843,584-2,933,787 |
| SCNN1A | Epithelial sodium channel α subunit | chr12: 6,454,011-6,486,390 |
| MMP3 | Matrix metallopeptidase 3 | chr11: 102,704,528-102,716,342 |
| ALR2 (AKR1B1) | Aldose reductase | chr7: 134,125,107-134,145,888 |

TABLE 7-continued

Gene names and sequences which interact to explain large variance of renal function in type 2 diabetes with renal function as a major predictor for cardiovascular disease.

| Gene label | Full name of gene | Genomic sequence corresponding to the cDNA sequence plus 2 kb upstream and downstream flanking sequences (GRCh37/hg19) |
|---|---|---|
| TNF | Tumor necrosis factor α | chr6: 31,541,350-31,548,110 |
| APOE | Apolipoprotein E | chr19: 45,407,039-45,414,649 |
| APOC3 | Apolipoprotein C III | chr11: 116,698,624-116,705,787 |
| IDE | Insulin degrading enzyme | chr10: 94,211,600-94,335,852 |
| CPE | Carboxypeptidase E | chr4: 166,298,097-166,421,481 |

TABLE 8

Clinical and biochemical characteristics and use of medications in a prospective cohort of Chinese type 2 diabetic patients stratified by cancer status during a median follow-up period of 5 years. Some of the data have been reported by Yang et al. *Diab Res Clin Pract*, 90: 343-51, 2010.

| | Patients without cancer (n = 5832) Median(IQR*) or % (n) | Patients with cancer (n = 271) Median(IQR*) or % (n) | P value |
|---|---|---|---|
| Baseline variables | | | |
| Age (year) | 57(20) | 66(15) | <.0001† |
| Male gender | 45.8%(2669) | 51.3%(139) | .0743‡ |
| Smoking status | | | <.0001‡ |
| Ex-smoker | 15.10%(878) | 18.7%(38) | |
| Current smoker | 14.8%(862) | 23.2%(47) | |
| Alcohol drinking status | | | <.0001‡ |
| Ex-drinker | 11.8%(688) | 21.0%(51) | |
| Current drinker | 7.3%(427) | 7.4%(20) | |
| Body mass index (kg/m²) | 24.8(4.9) | 24.3(4.7) | .1296† |
| Duration of diabetes (year) | 6(9) | 8(10) | .0202† |
| Systolic BP (mmHg) | 134(27) | 137(25) | .0011† |
| Diastolic BP (mmHg) | 75(14) | 75(16) | .6152† |
| Glycated hemoglobin (%) | 7.2(2.0) | 7.4(2.3) | .3586† |
| LDL-C (mmol/L) | 3.10(1.23) | 3.10(1.30) | .8872† |
| HDL-C (mmol/L) | 1.26(0.43) | 1.25(0.51) | .3846† |
| Triglyceride (mmol/L) | 1.34(1.02) | 1.23(0.77) | .0014† |
| Total cholesterol (mmol/L) | 5.10(1.33) | 5.00(1.42) | .3083† |
| ACR (mg/mmol) | 2.06(10.47) | 3.45(14.18) | .0023† |
| eGFR (ml min$^{-1}$ 1.73 m$^{-2}$) | 103.1(41.6) | 98.8(37.3) | .0184† |
| Prior myocardial infarction | 2.0%(114) | 2.6%(7) | .4683¶ |
| Prior stroke | 4.5%(261) | 3.7%(10) | .5396‡ |
| Death (all-cause) during follow-up | 6.3%(369) | 50.2%(163) | <.0001‡ |
| Use of medications 2.5 yr prior to enrolment | | | |
| Statins | 15.5%(903) | 10.3%(28) | .0211‡ |
| Fibrates | 4.5%(261) | 3.3%(9) | .3664‡ |
| ACEIs/ARBs | 29.5%(1718) | 28.8%(78) | .8114‡ |
| Insulin | 23.9%(1394) | 25.8%(70) | 4676‡ |
| Metformin | 56.6%(3303) | 52.4%(142) | .1691‡ |
| Sulphonylurea | 62.4%(3640) | 63.5%(172) | .7260‡ |
| TZDs | 0.5%(28) | 0.4%(1) | .7949‡ |
| Use of medications during follow-up§ | | | |
| Statins | 38.6%(2249) | 22.5%(61) | <.0001‡ |
| Fibrates | 10.2%(595) | 5.9%(16) | .0212‡ |
| ACEIs/ARBs | 57.9%(3378) | 52.4%(142) | .0720‡ |
| Insulin | 37.7%(2197) | 36.2%(98) | .6161‡ |
| Metformin | 74.5%(4347) | 63.8%(173) | <.0001‡ |
| Sulphonylurea | 71.3%(4160) | 69.4%(188) | .4864‡ |
| TZDs | 6.8%(398) | 0.7%(2) | <.0001‡ |

Abbreviations: IQR, interquartile range; BP: blood pressure; LDL-C, low-density lipoprotein cholesterol; HDL-C, high-density lipoprotein cholesterol; ACR, spot urine albumin:creatinine ratio; eGFR, estimated glomerular filtration rate; ACEIs, angiotensin-converting enzyme inhibitors; ARBs, angiotensin II receptor blockers, RAS, renin-angiotensin system; TZD, Thiazolidinedione;
†Derived from the Wilcoxon two-sample test;
‡Derived from Chi-square test;
¶Derived from the Fisher's exact test;
§Including use started on or before enrolment but continued during follow-up period.

TABLE 9

Hazard ratios of drug use for cancer in a 5-year prospective cohort of Chinese type 2 diabetic patients enrolled in the Hong Kong Diabetes Registry. Refer to Chan et al *Curr Cardiovasc Risk Rep*; 5: 230-9, 2011 for background and data structure of the Hong Kong Diabetes Registry.

| Users versus non user | No. of sample size | No. of events | HR(95% CI) | P value |
|---|---|---|---|---|
| ACEIs or ARBs among those who did not use ACEIs or ARBs 2.5 yr prior to enrolment | | | | |
| Model 1 | 4307 | 199 | 0.38(0.27-0.53) | <.00001 |
| Model 2 | 4307 | 199 | 0.55(0.39-0.78) | .000 |
| Statins among those who did not use statins 2.5 yr prior to enrolment | | | | |
| Model 1 | 5172 | 243 | 0.36(0.24-0.53) | <.0001 |
| Model 2 | 5172 | 243 | 0.47(0.31-0.70) | .0003 |

TABLE 9-continued

Hazard ratios of drug use for cancer in a 5-year prospective cohort of
Chinese type 2 diabetic patients enrolled in the Hong Kong Diabetes Registry.
Refer to Chan et al *Curr Cardiovasc Risk Rep*; 5: 230-9, 2011 for background
and data structure of the Hong Kong Diabetes Registry.

| Users versus non user | No. of sample size | No. of events | HR(95% CI) | P value |
|---|---|---|---|---|
| Insulin among those who did not use insulin 2.5 yr prior to enrolment | | | | |
| Model 1 | 4639 | 201 | 0.48(0.31-0.73) | .0006 |
| Model 2 | 4639 | 201 | 0.58(0.38-0.89) | .0119 |
| Metformin among those who did not use metformin 2.5 yr prior to enrolment | | | | |
| Model 1 | 2658 | 129 | 0.38(0.25-0.56) | <.0001 |
| Model 2 | 2658 | 129 | 0.39(0.25-0.61) | <.0001 |
| Sulphonylurea among those who did not use sulphonylurea 2.5 yr prior to enrolment | | | | |
| Model 1 | 2291 | 99 | 0.45(0.29-0.72) | .0008 |
| Model 2 | 2291 | 99 | 0.44(0.27-0.73) | .0014 |
| TZDs among those who did not use TZDs 2.5 yr prior to enrolment | | | | |
| Model 1 | 6074 | 270 | 0.12(0.03-0.50) | .0033 |
| Model 2 | 6074 | 270 | 0.18(0.04-0.72) | .0153 |

Model 1 adjusted for propensity scores (c-statistics = 0.80 for ACEIs or ARBs; 0.80 for statins; 0.79 for insulin; 0.73 for metformin; 0.66 for sulphonylurea; and 0.74 for TZDs), estimated using logistic regression procedures with age, sex, BMI, LDL-C, HDL-C, triglyceride, smoking status, alcohol use, HbA1c, SBP, Ln_ACR, estimated GFR, duration of disease, PAD, retinopathy, neuropathy, prior MI and stroke as independent variables; Model 2 adjusted for LDL-C related risk indicator, nonlinear associations of HDL-C and triglyceride, BMI (<24, ≥27.6 kg/m2), age, sex, occupation, use of alcohol and tobacco, disease duration, SBP, use of statins, ACEIs/ARBs, fibrates, sulphonyluria, metformin and TZDs during follow-up period as well as propensity score of these drugs.

---

What is claimed is:

1. A method for reducing risk of type 2 diabetes in a subject, comprising the steps of:
   (a) performing a polymerase chain reaction (PCR) to determine nucleotide sequence of at least a portion of genomic sequence of carboxypeptidase E (CPE) present in a biological sample taken from the subject,
   (b) detecting a G allele in polymorphism rs1583645,
   (c) determining the subject as having an increased risk of developing type 2 diabetes based on a G allele being detected in polymorphism rs1583645, and
   (d) administering to the subject who is determined in step (c) as having an increased risk of developing type 2 diabetes a medicine to reduce risk of onset of diabetes.

2. The method of claim 1, wherein the sample is a blood or saliva sample.

3. The method of claim 1, wherein the subject is of Asian descent.

4. The method of claim 1, wherein the subject has a BMI no greater than 25 kg/m$^2$.

5. The method of claim 1, wherein the subject has a family history of type 2 diabetes but has not been diagnosed with type 2 diabetes.

6. The method of claim 1, wherein the medicine comprises a cholesterol lowering drug or a blood glucose lowering drug.

7. The method of claim 1, further comprising determining nucleotide sequence of at least a portion of genomic sequence of one or more of LIPC, LPL, CETP, PPARG, GNB3, NOS3, LTA, AGTA1, ADRB2, ADRB3, NPPA, ADD1, SCNN1A, MMP3, ALR2, TNF, APOE, and APOC3 genes present in the sample.

8. The method of claim 1, further comprising:
   in step (b) detecting a C allele in polymorphism rs10021007 for CPE,
   wherein in step (c) the subject is determined as having an increased risk of developing type 2 diabetes based on a G allele being detected in polymorphism rs1583645 and a C allele being detected in polymorphism rs10021007.

9. The method of claim 1, further comprising:
   in step (a) performing a polymerase chain reaction (PCR) to determine nucleotide sequence of at least a portion of genomic sequence of insulin degrading enzyme (IDE) present in the biological sample; and
   in step (b) detecting a C allele in polymorphism rs6583813 for IDE,
   wherein in step (c) the subject is determined as having an increased risk of developing type 2 diabetes based on a G allele being detected in polymorphism rs1583645 and a C allele being detected in polymorphism rs6583813.

10. The method of claim 8, further comprising:
    in step (a) performing a polymerase chain reaction (PCR) to determine nucleotide sequence of at least a portion of genomic sequence of insulin degrading enzyme (IDE) present in the biological sample; and
    in step (b) detecting a C allele in polymorphism rs6583813 for IDE,
    wherein in step (c) the subject is determined as having an increased risk of developing type 2 diabetes based on a G allele being detected in polymorphism rs1583645 and a C allele being detected in polymorphism rs10021007 and a C allele being detected in polymorphism rs6583813.

11. The method of claim 1, wherein the medicine is metformin, an alpha glucosidase inhibitor, or a lipase inhibitor.

* * * * *